United States Patent [19]

Pieper et al.

[11] Patent Number: 5,028,224
[45] Date of Patent: Jul. 2, 1991

[54] APPARATUS FOR INTERMITTENTLY DEPOSITING PARTICULATE MATERIAL IN A SUBSTRATE

[75] Inventors: Christopher M. Pieper, Neenah; Jeffrey W. King, Appleton; Bruce R. Shafer, Green Bay; Robert A. Stevens; Timothy L. Wehman, both of Appleton; Edward E. Werner, Oshkosh, all of Wis.

[73] Assignee: Kimberly-Clark Corporation, Neenah, Wis.

[21] Appl. No.: 462,363

[22] Filed: Jan. 9, 1990

[51] Int. Cl.⁵ .......................... B01D 45/12; B28B 5/00
[52] U.S. Cl. .................. 425/80.100; 19/304; 55/461; 264/40.1; 264/113; 264/518; 425/135
[58] Field of Search ............... 264/40.1, 40.7, 113, 264/518, DIG. 75; 425/80.1, 81.1, 83.1, 100, 103, 135, 82.1; 19/304; 28/118, 119; 65/9; 55/461

[56] References Cited

U.S. PATENT DOCUMENTS

| | | | |
|---|---|---|---|
| 5,422 | 2/1848 | Lafitte | 55/461 |
| Re. 29,789 | 10/1978 | Kolbach | 604/365 |
| 1,838,117 | 12/1931 | Simms et al. | 55/461 |
| 2,696,911 | 12/1954 | Umney | 55/461 |
| 2,720,005 | 10/1955 | Clark et al. | 425/83.1 |
| 3,187,387 | 6/1965 | Schuller | 65/9 |
| 3,220,811 | 11/1965 | Schuller | 65/9 |
| 3,442,633 | 5/1969 | Perry | 65/9 |
| 3,482,287 | 12/1969 | Flewwelling | 264/518 |
| 3,669,103 | 6/1972 | Harper et al. | 604/368 |
| 3,670,731 | 6/1972 | Harmon | 604/368 |
| 3,757,367 | 10/1973 | Campbell | 55/461 |
| 3,792,943 | 2/1974 | Helgesson | 264/518 |
| 3,860,002 | 1/1975 | Kolbach | 604/365 |
| 3,888,257 | 6/1975 | Cook et al. | 604/368 |
| 3,968,798 | 7/1976 | Hokanson | 604/368 |
| 3,984,272 | 10/1976 | Teed | 156/201 |
| 4,087,506 | 5/1978 | Cook et al. | 264/112 |
| 4,111,671 | 9/1978 | Williamson | 55/461 |
| 4,144,886 | 3/1979 | Holst et al. | 604/368 |
| 4,217,900 | 8/1980 | Wiegner et al. | 604/376 |
| 4,333,462 | 6/1982 | Holtman et al. | 604/368 |
| 4,333,463 | 6/1982 | Holtman | 604/368 |

(List continued on next page.)

FOREIGN PATENT DOCUMENTS

| | | |
|---|---|---|
| 0325416 | 7/1989 | European Pat. Off. |
| WO88/04165 | 6/1988 | PCT Int'l Appl. |
| 1406615 | 9/1975 | United Kingdom |
| 2150033A | 6/1985 | United Kingdom |

OTHER PUBLICATIONS

Technical Bulletin entitled "SAP Sheet" dated Oct., 1982 issued by Sanyo Chemical Industries.

*Primary Examiner*—Jay H. Woo
*Assistant Examiner*—Robert B. Davis
*Attorney, Agent, or Firm*—Paul Yee

[57] ABSTRACT

An apparatus for forming a zoned distribution of particulate material within a fibrous web includes a conveying mechanism for providing a gas entrained supply of the particulate material and a segregating mechanism for centrifugally directing at least a portion of the particulate material into an accumulation region of the apparatus. A transferring mechanism selectively directs particulate material from the accumulation region into a delivery gas stream to provide an intermittent flow volume of a selected quantity of particulate material from the accumulation region through a delivery conduit and into a web forming chamber. A fiberizing mechanism provides a flow of a selected fibrous material into the web forming chamber, and a directing mechanism controls the intermittent flow of particulate material from the delivery conduit into the forming chamber. A foraminous forming layer is disposed within the forming chamber for receiving the fibrous material and the particulate material to produce a fibrous web which includes zoned regions having selected, different amounts of the particulate material therein.

24 Claims, 25 Drawing Sheets

U.S. PATENT DOCUMENTS

| | | | |
|---|---|---|---|
| 4,340,556 | 7/1982 | Ciencewicki | 264/119 |
| 4,381,782 | 5/1983 | Mazurak et al. | 604/368 |
| 4,381,783 | 5/1983 | Elias | 604/368 |
| 4,388,056 | 6/1983 | Lee et al. | 425/83.1 |
| 4,410,324 | 10/1983 | Sabee | 604/368 |
| 4,461,621 | 7/1984 | Karami et al. | 604/368 |
| 4,468,428 | 8/1984 | Early et al. | 428/221 |
| 4,551,191 | 11/1985 | Kock et al. | 156/276 |
| 4,557,777 | 12/1985 | Sabee | 156/201 |
| 4,585,448 | 4/1986 | Enloe | 604/378 |
| 4,650,479 | 3/1987 | Insley | 604/358 |
| 4,673,402 | 6/1987 | Weisman et al. | 604/368 |
| 4,675,209 | 6/1987 | Pedigrew | 427/194 |
| 4,685,915 | 8/1987 | Hasse et al. | 604/378 |
| 4,699,619 | 10/1987 | Bernardin | 604/378 |
| 4,699,823 | 10/1987 | Kellenberger et al. | 428/219 |
| 4,712,277 | 12/1987 | Gustavsson | 19/304 |
| 4,715,918 | 12/1987 | Lang | 156/273.1 |
| 4,718,901 | 1/1988 | Singheimer | 604/385 |
| 4,762,521 | 8/1988 | Roessler et al. | 604/38 SA |
| 4,764,325 | 8/1988 | Angstadt | 264/113 |
| 4,765,780 | 8/1988 | Angstadt | 406/123 |
| 4,778,459 | 10/1988 | Fuisz | 604/378 |
| 4,800,102 | 1/1989 | Takada | 427/197 |
| 4,834,735 | 5/1989 | Alemany et al. | 604/368 |
| 4,904,440 | 2/1990 | Angstadt | 264/113 |
| 4,908,175 | 3/1990 | Angstadt | 264/113 |
| 4,921,650 | 5/1990 | Eriksson et al. | 264/518 |
| 4,927,582 | 5/1990 | Bryson | 264/113 |

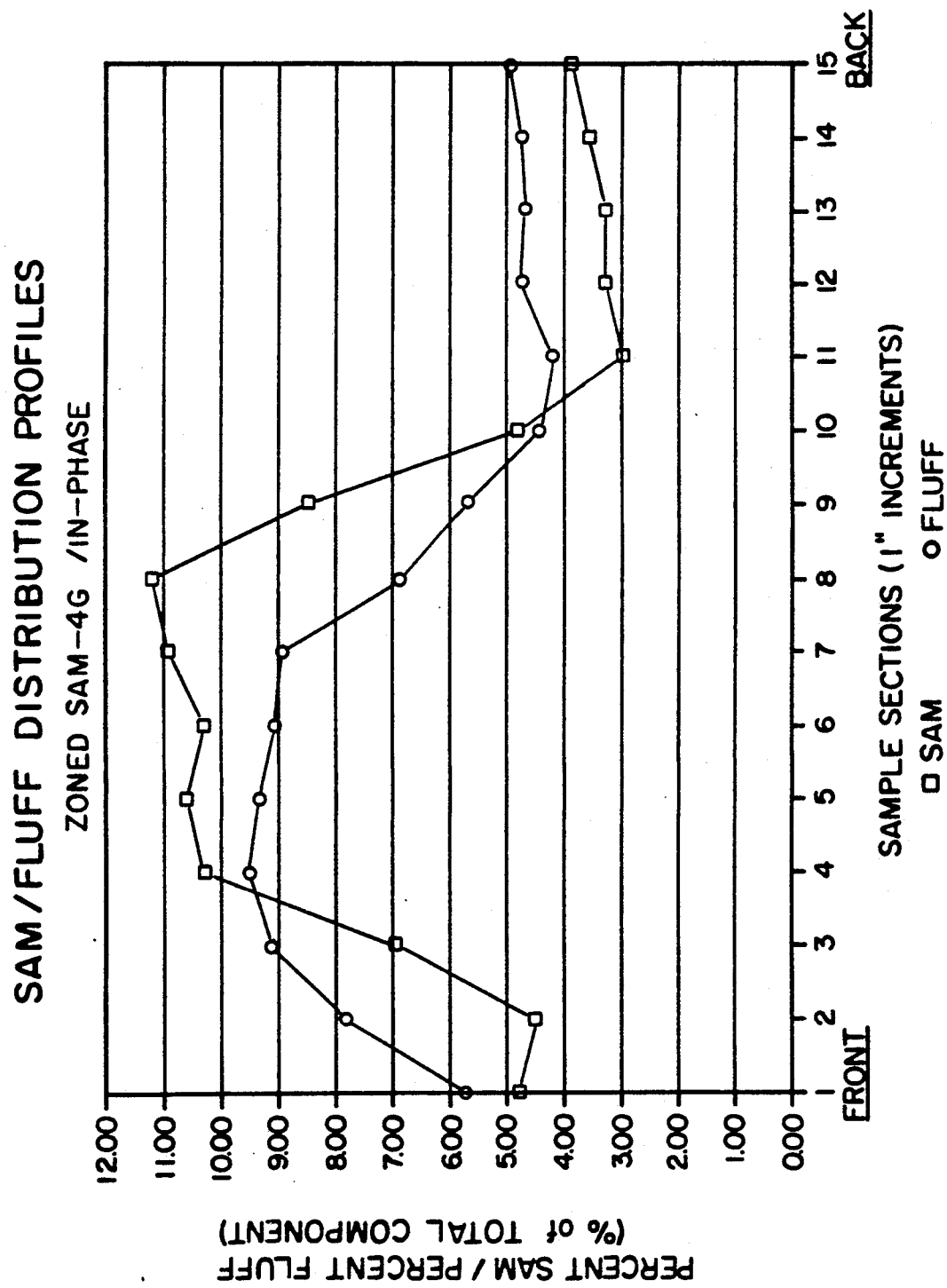

APPARATUS FOR INTERMITTENTLY DEPOSITING PARTICULATE MATERIAL IN A SUBSTRATE

THE FIELD OF THE INVENTION

The present invention relates to a method and apparatus for forming a zoned distribution of particulate material within a fibrous web. More particularly, the present invention relates to a method and apparatus for forming a zoned distribution of superabsorbent polymer particles within an absorbent pad composed of hydrophilic fibers.

BACKGROUND OF THE INVENTION

Absorbent articles, such as disposable infant diapers, feminine care products, incontinence garments and the like, have included high absorbency superabsorbent polymers to increase the absorbent capacity of the article and to reduce the bulkiness of the article. For example, see U.S. Pat. No. 3,669,103 to Harper, U.S. Pat. No. 3,670,731 to Harmon, and U.S. Pat. No. 4,087,506 to Cook et al. Particular absorbent article designs have concentrated superabsorbent polymers in selected regions of the absorbent pad. For example, see U.S. Pat. No. 4,381,782 to Mazurak et al., U.S. Pat. No. 4,410,324 to Sabee and U.S. Pat. No. 4,461,621 to Karami et al. In some of these conventional arrangements, the high absorbency material, such as superabsorbent polymer, have been substantially uniformly mixed with absorbent fibers located within selected layers, or strips. In other arrangements, the high absorbency material has been substantially isolated in layers, zones or pockets within the absorbent pad with the high absorbency material substantially unmixed with the absorbent fibers.

Various devices and processes have been employed to manufacture absorbent article designs. Air forming techniques for forming webs of hydrophilic fibers, such as woodpulp fibers, are well known in the art. In addition, it is well known that superabsorbent polymers may be mixed with the hydrophilic fibers during an airlaying process to form an absorbent web. For example, see the Sanyo Technical Bulletin entitled "SAP SHEET", dated October 1982.

Particular absorbent article designs have particles of superabsorbent polymer localized in selected regions. For example, U.S. Pat. No. 3,888,257 issued June 10, 1975 to R. Cook et al. describes a disposable absorbent article in which a rectilinear, central zone of a matrix of fiberized woodpulp incorporates a 3-dimensional dispersion of hydro-colloid polymer particles. U.S. Pat. No. 4,381,782 issued May 3, 1983 to P. Mazurak et al. describes an absorbent article wherein hydrogel material is incorporated by placement near a front edge of an absorbent batt in a diaper article. Other designs have incorporated superabsorbent materials within selected layers, longitudinal strips, lateral strips and other types of isolated zones or regions.

Various methods and apparatus have been employed to manufacture absorbent articles. For example, U.K. Patent Application, GB 2,150,033 A published June 26, 1985, describes a suction drum apparatus for making an absorbent pad wherein an integrated shell of flocculent material surrounds an internal absorbent layer. U.S. Pat. No. 4,087,508 issued May 2, 1978 to R. Cook et al. describes a method which includes applying hydrocolloid polymer particles onto the surface of a central zone of a moving web, and distributing the applied particles into the body of the moving web by air-pressure means. International Patent Application No. WO 88/04165 published 16 June 1988 described a method and apparatus for forming a nonwoven pad consisting of fibrous material in which highly moisture-absorbent particles are intermixed with the fibrous material throughout a predetermined portion of the thickness of the nonwoven pad. A spray gun or an extension thereof is positioned within the chamber relative to the fibrous material atop a conveyor and is operated to discharge moisture-absorbent material at a predetermined velocity, such that the moisture-absorbent material is intermixed with the fibrous material throughout a central layer of the thickness of the nonwoven pad while forming boundary layers on either side of the center layer which are substantially free of moisture-absorbent material. The spray gun preferably operates intermittently to form spaced, sharply defined areas along the length and width of the nonwoven pad wherein each area has moisture absorbent material interspersed throughout a portion of the thickness thereof.

Conventional methods and apparatus, such as those described above, have not been sufficiently satisfactory. For example, the devices may be overly complex and expensive and may not provide desired patterns of deposition for particulate materials, such as superabsorbent granules. The rate of delivery of the superabsorbent particles may not be adequately controlled, and the systems may be excessively sensitive to changing bulk densities in the particulate material.

BRIEF DESCRIPTION OF THE INVENTION

The present invention provides a distinctive technique for forming a zoned distribution of particulate material within a fibrous web. Generally stated, an apparatus of the invention comprises conveying means for providing a gas entrained supply stream of the particulate material, and segregating means for centrifugally directing at least a portion of the particulate material into an accumulation region of the apparatus. Transferring means selectively direct particulate material from the accumulation region into a delivery gas stream to provide an intermittent flow of a selected quantity of particulate material from the accumulation region through a delivery conduit and into a web forming chamber. Fiberizing means provide a flow of a selected fibrous material into the web forming chamber, and directing means control the intermittent flow of particulate material from the delivery conduit into the forming chamber. A foraminous forming layer is disposed within the forming chamber for receiving the fibrous material and the particulate material to form a fibrous web which includes zoned regions having selected, different amounts of the particulate material therein.

The present invention can further provide a method for forming a zoned distribution of particulate material within a fibrous web. In this aspect of the invention, the method comprises the steps of providing a gas entrained supply stream of the particulate material, and centrifugally directing at least a portion of the particulate material into an accumulation region. The particulate material is selectively transferred from the accumulation region into a delivery gas stream to provide an intermittent flow of a selected quantity of particulate material from the accumulation region through a delivery conduit and into a web forming chamber. A flow of a selected fibrous material is provided into the web forming chamber, and the intermittent flow of particulate material from the delivery conduit into the forming chamber is selectively controlled. The fibrous material and particulate material are received on a foraminous forming layer located within the forming chamber to produce a fibrous web which includes zoned regions having selected, different amounts of the particulate material therein.

Yet another aspect of the invention is a distinctive absorbent article comprising a substantially unitary web composed of a mass of hydrophilic fibers, and a quantity of superabsorbent polymer particles located within the fibrous mass. The superabsorbent particles have a distinctive, nonuniform distribution along a longitudinal, length dimension of the web. The weight percentage of superabsorbent (per unit weight of the combined particles and fiber) is also nonuniformly distributed along the length dimension. In particular aspects of the invention, the article can include a longitudinal, length-wise particle distribution which is substantially configured in the form of two or more stepped stages.

The present invention can advantageously provide a method and apparatus which, when compared to conventional devices, can more efficiently localize particulate material within selected regions of a fibrous web, and can position the particulate material in a manner which is generally independent of the flow of fibrous material employed to form the web. As a result, the present invention can advantageously provide an air-laid, intermingled structure wherein larger proportions of particles can be placed at selected locations without concomitantly placing larger proportions of fibrous material at those locations. The apparatus can also have lower complexity and lower costs while affording sufficient controllability to provide desired patterns of particulate distribution within the fibrous web. In particular aspects of the invention, the method and apparatus can provide lower weight variability between individual quantities of delivered particulate material and can advantageously be arranged to automatically detect problems within the system. In other aspects of the invention, the method and apparatus can be less sensitive to the flow characteristics of the particulate material and can advantageously be configured to have fewer transient flow conditions caused by repetitively accelerating and/or decelerating the flow of particulate material. Difficulties in adequately controlling transient flow conditions may cause undesired variations in the amount of material contained in the individual particulate quantities. A further advantage of the invention is that the method and apparatus can operate at high speeds. For example, the method and apparatus may be configured to deliver 600 or more substantially discrete quantities of particulate material per minute.

The distinctive absorbent article of the invention can advantageously provide a more efficient use of the absorbent material and provide a more effective, localized placement of superabsorbent particles within a web or pad composed of hydrophilic fibers. In addition, the absorbent article of the invention may advantageously incorporate a selectively zoned placement of two or more different types of particulate material. For example, the article may include two or more different types of superabsorbent material, each of which has a distinctive set of absorption characteristics and is differently located within a fibrous web.

BRIEF DESCRIPTION OF THE DRAWINGS

The present invention will be more fully understood and further advantages will become apparent when reference is made to the following detailed description of the invention and the drawings, in which:

FIGS. 17 and 17A show graphic representations of regions along the length of an article of the invention wherein article regions with higher amounts of superabsorbent are in-phase with the article regions with higher amounts of fibrous material;

DETAILED DESCRIPTION OF THE INVENTION

The following detailed description will be made in the context of depositing superabsorbent particles within a web employed to construct an absorbent body for use in a disposable diaper article. It should be understood, however, that the present invention may also be employed to incorporate other types of particulate material within a mass of hydrophilic or hydrophobic fibers. In addition, it should be readily understood that the present invention may also be employed to produce absorbent bodies for other types of absorbent articles, such as feminine care products, incontinence garments and the like. All of such alternative configurations are contemplated as being within the scope of the present invention.

The invention is particularly useful for depositing particles of organic or inorganic high-absorbency (e.g. superabsorbent) material within a fibrous web. Suitable inorganic high-absorbency materials include, for example, absorbent clays and silica gels. Organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to impart desired levels of water insolubility to the material. Crosslinking may, for example, be by irradiation or by covalent, ionic, Van der Waals, or hydrogen bonding. Suitable materials are available from various commercial vendors, such as Dow Chemical Company, Hoechst Celanese Corporation, Allied-Colloid, and Stockhausen. Typically, the high-absorbency material is capable of absorbing at least about 15 times its weight in water, and preferably is capable of absorbing at least about 25–50 times its weight in water.

The particles of high absorbency material may have regular shapes or irregular shapes, such as elongated forms. For example, particles of high-absorbency material may be configured in the form of granules, flakes, fibers, or the like. The particles typically measure about 50–1000 micrometers in size, preferably measure about 100–800 micrometers, and more preferably measure about 200–600 micrometers in size to provide improved processability through the apparatus of the invention.

Figure 1:
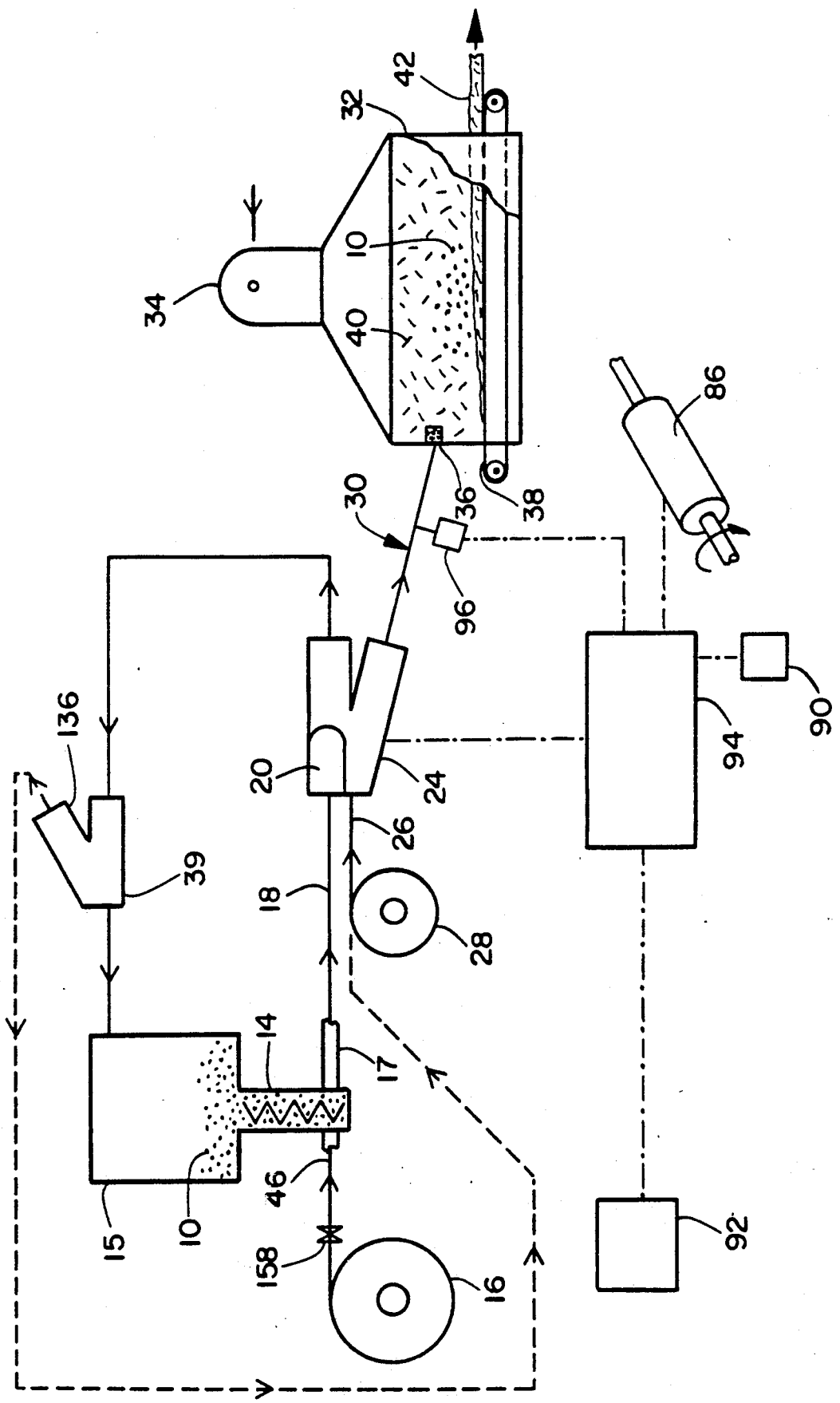
FIG. 1 representatively shows a schematic, system diagram of the invention.

With reference to FIG. 1, a representative apparatus of the invention is configured to form a zoned distribution of particulate material, such as particles 10 of a superabsorbent polymer material (SAM), within a fibrous web 42, such as a web comprising woodpulp fluff fibers. A conveying means, such as a mechanism composed of particle feeder 14 and conveying blower 16, provides a gas entrained supply stream of superabsorbent polymer particles. A segregating means 20 centrifugally directs at least a portion of the particulate material into an accumulation region of the apparatus. Transferring means 24 selectively directs the particulate material from the accumulation region into a delivery gas stream 26 supplied by delivery blower 28 to provide a time-varying, intermittent flow of selected, controlled quantities of particulate material from the accumulation region through a delivery conduit 30 into a web forming chamber 32. Fiberizing means, such as hammermill 34 provides a flow of a selected fibrous material, such as woodpulp fluff fibers, into the web forming chamber. A directing means, such as delivery nozzle 36, controls the intermittent flow of superabsorbent particles from delivery conduit 30 into forming chamber 32, and a foraminous forming layer 38 is moveable and disposed within the forming chamber to receive fluff fibers 40 and particles 10 thereon to form fibrous web 42. The fibrous web includes distinctive, zoned regions having selected, different amounts of particulate material therein. The supply stream of gas/particles can be recirculated to feeder device through a suitable conduit, and a particle recovery system 39 may be employed to separate the particles from the gas for return into a supply reservoir of the feeder device. The residual gas exits from the recovery system through gas exhaust section 136.

The method and apparatus of the invention can advantageously operate at high speeds. For example, the method and apparatus may be configured to deliver 600 or more substantially discrete quantities of particulate material per minute, and in particular embodiments, the invention can be configured to deliver at least 1000 substantially discrete quantities of particulate material per minute.

The illustrated embodiment of the invention is shown as having a conveying blower 16 and delivery blower 28 which are physically separate from each other. It should be readily appreciated, however, that the separate functions provided by the conveying blower and delivery blower may be provided by a single, combined mechanism, such as a single blower. For example, the residual gas exiting from exhaust section 136 of recovery system 39 may be recirculated with suitable connecting conduits (dashed line of arrows) to provide delivery gas stream 26. Accordingly, the delivery gas stream may be composed of the residual gas stream from recovery system 39. With this arrangement, blower 28 may be eliminated, and blower 16 may advantageously be employed to generate both conveying gas stream 46 and delivery gas stream 26 in a more efficient system.

Feeder device 14 includes a particulate regulating means for providing a selected mass flow rate of high absorbency particles, such as particles composed of superabsorbent hydrogel polymer, into a conveying gas stream 46 provided by conveying blower 16. It should be readily understood that the amount of superabsorbent polymer delivered into conveying gas stream 46 is dependent upon the forming rate of web 42 and the weight percent of particles desired to be contained within the web. In the illustrated embodiment, the particulate regulating means is constructed and configured to provide a particulate mass flow rate which is within the range of about 6–90 gm/sec. Various types of feeder mechanisms may be employed with the present invention. Preferably, the invention employs a "weight-in loss" type of feeder system which can take into account the amount of polymer being returned into reservoir 15 from particle recovery system 39 and automatically adjust the amount of polymer being fed into supply stream 18. This device can thereby help control the delivery of the desired amounts of polymer into web 42. In the shown embodiment, the feeder device may be a LWF3-35 feeder manufactured by K-tron Corp., a company located in Pitman, N.J. Other equivalent devices may also be employed with the present invention.

Various types of commercially available blower devices may be employed with the present invention. In the shown embodiment, conveying blower 16 may be a VB-019 blower manufactured by Spencer Turbine, a company located in Windsor, Conn.

In particular embodiments of the invention, conveying blower 16 is configured to supply a conveying gas flow velocity of not less than about 5 m/sec (about 1000 ft/min), and preferably provides a gas velocity of not less than about 9 m/sec (about 1800 ft/min). In other embodiments of the invention, conveying blower 16 is configured to provide a gas velocity in conveying gas stream 46 of not more than about 35 m/sec (about 7000 ft/min), and preferably provides a velocity of not more than about 45 m/sec (about 8500 ft/min) to provide improved performance. A suitable conveying conduit 17 is employed to transport the particle/gas mixture composed of the superabsorbent particles entrained in the moving stream of conveying gas.

Proper conveying gas flow is dependent on the material being conveyed. In addition to the velocity ranges given, it is desirable to maintain the "solids loading ratio" (mass flow rate of material divided by the mass flow rate of conveying gas) below about 5. Preferably, the solids loading ratio is maintained below about 3. At these ratios, the resultant two-phase flow is typically classified as "lean phase". Lean phase flow is desirable to minimize short-term weight variability.

Figure 2:
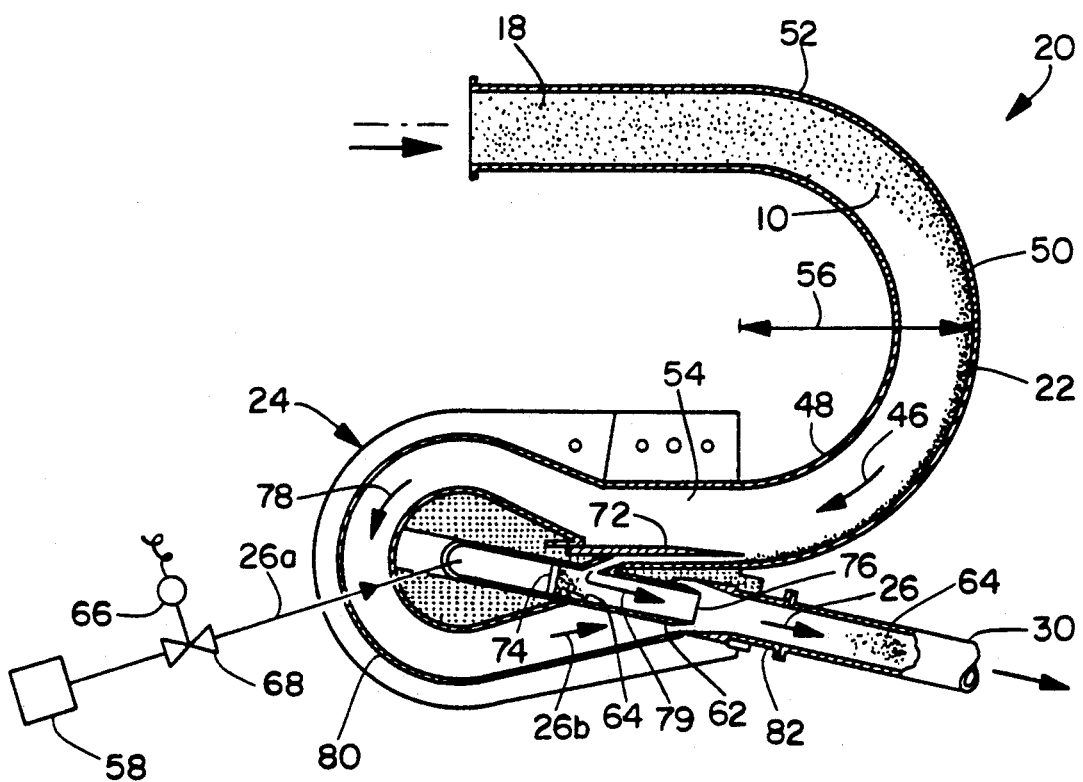
FIG. 2 representatively shows an embodiment of the invention which includes a pulsing mechanism for producing an intermittent flow of particles.

Referring now to FIG. 2, particulate/gas supply stream 18 moves into a segregating means 20 for centrifugally directing at least a portion of the superabsorbent particles 10 into an accumulation region 22 of the apparatus. In the illustrated embodiment, the segregating means includes an arcuate, curved conduit 48 having a radiused bend through which supply stream 18 moves to operably concentrate the superabsorbent particles in an accumulation region comprising a zone located toward a radially outward wall 50 of the curved conduit. Within supply stream 18, the superabsorbent particles may be randomly or substantially uniformly distributed within the entraining stream of moving transport gas. As the particle/gas mixture moves through the curved path provided by conduit 48, the momentum and dynamic inertia ("centrifugal force") of the moving particles causes the particles to displace the less dense conveying air and hug outward wall 50. The particles concentrate along wall 50 as the wall provides the centripetal force needed to accelerate and bend the movement of the particles along the curved path defined by conduit 48. As a result, particles 10 are operably segregated toward the radially outward wall 50 of the curved conduit.

In a particular aspect of the invention, curved conduit 48 traverses a curved, generally circular arc subtended by an angle of not less than about 30 degrees, and preferably traverses an arc subtended by an angle of not less than about 60 degrees. In a further aspect of the invention, curved conduit 48 traverses a curved, substantially circular arc subtended by an angle of not more than about 360 degrees, and preferably traverses an arc subtended by an angle of not more than about 300 degrees to provide desired advantages.

Curved conduit 48 has an inlet section 52 and an outlet section 54. Supply stream 18 enters through inlet 52 and the residual supply stream departs the curved conduit from outlet section 54. Depending upon the particular operating condition of the segregating means, the residual supply stream may contain lesser amounts of superabsorbent particles than the original supply stream entering inlet section 52.

Where curved conduit 48 traverses an arc of greater than 180 degrees, it will be appreciated that there may be a crossing of the paths defined by inlet section 52 and outlet section 54. Accordingly, the inlet and outlet sections of conduit 48 may need to be physically offset from each other to avoid interference. Such a configuration may cause curved conduit 48 to define a generally "cork-screw", approximately helical path. For the purposes of the present invention, such a path shape is contemplated as being included within the meaning of the term, circular.

Figure 7A:
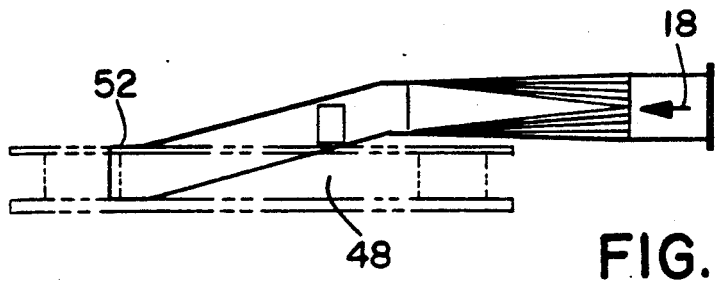
FIGS. 7, 7A and 7B respectively show representative side, top and end views of a "doughnut" configuration of the segregating mechanism of the invention.
Figure 7:
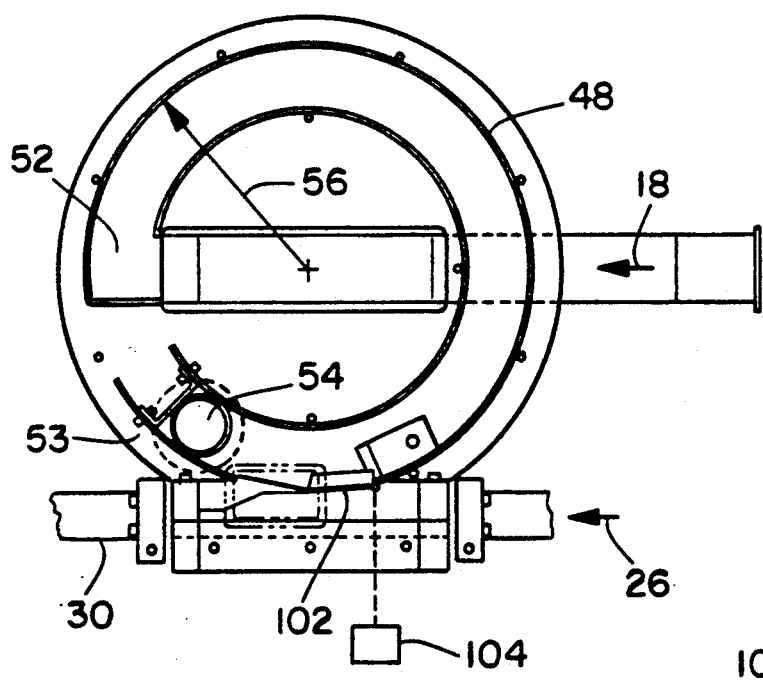
Figure 7B:
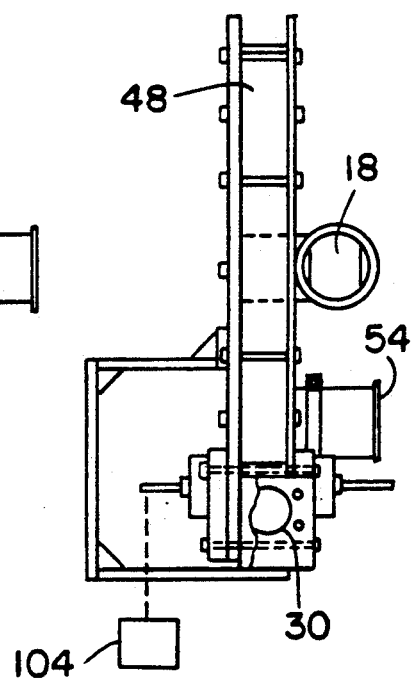

Another embodiment of the invention, representatively shown in FIGS. 7, 7A and 7B, comprises a curved conduit 48 configured in a generally "doughnut" shape. In the illustrated embodiment, the curved conduit is circular and includes a dividing wall member 53, which operably separates inlet section 52 from outlet section 54. The openings communicating into inlet section 52 and out from outlet section 54 may be arranged in any operable configuration. For example, supply stream 18 may enter inlet section 52 and exit outlet section 54 through the sides of the doughnut-shape, along directions which are generally perpendicular to the plane defined by the doughnut-shape. Alternatively, supply stream 18 may enter the inlet section (as illustrated) or exit the outlet section (not as illustrated) along a direction generally aligned with a radius of the doughnut-shape.

Curved conduit 48, in particular aspects of the invention, has a radius of curvature 56 of not less than about 5.08 cm (about 2 in), and preferably has a radius of curvature of not less than about 13 cm (about 5 in). In addition, the curved conduit has a radius of curvature of not more than about 5 m (about 197 in), and preferably has a radius of curvature of not more than about 1 m (about 39 in) to provide improved effectiveness. The shown embodiment of the invention has a radius of curvature about 15 cm (about 6 in) as determined by measuring from the focus or center of curvature out to the radially outward wall 50 of the curved conduit.

Figure 3:
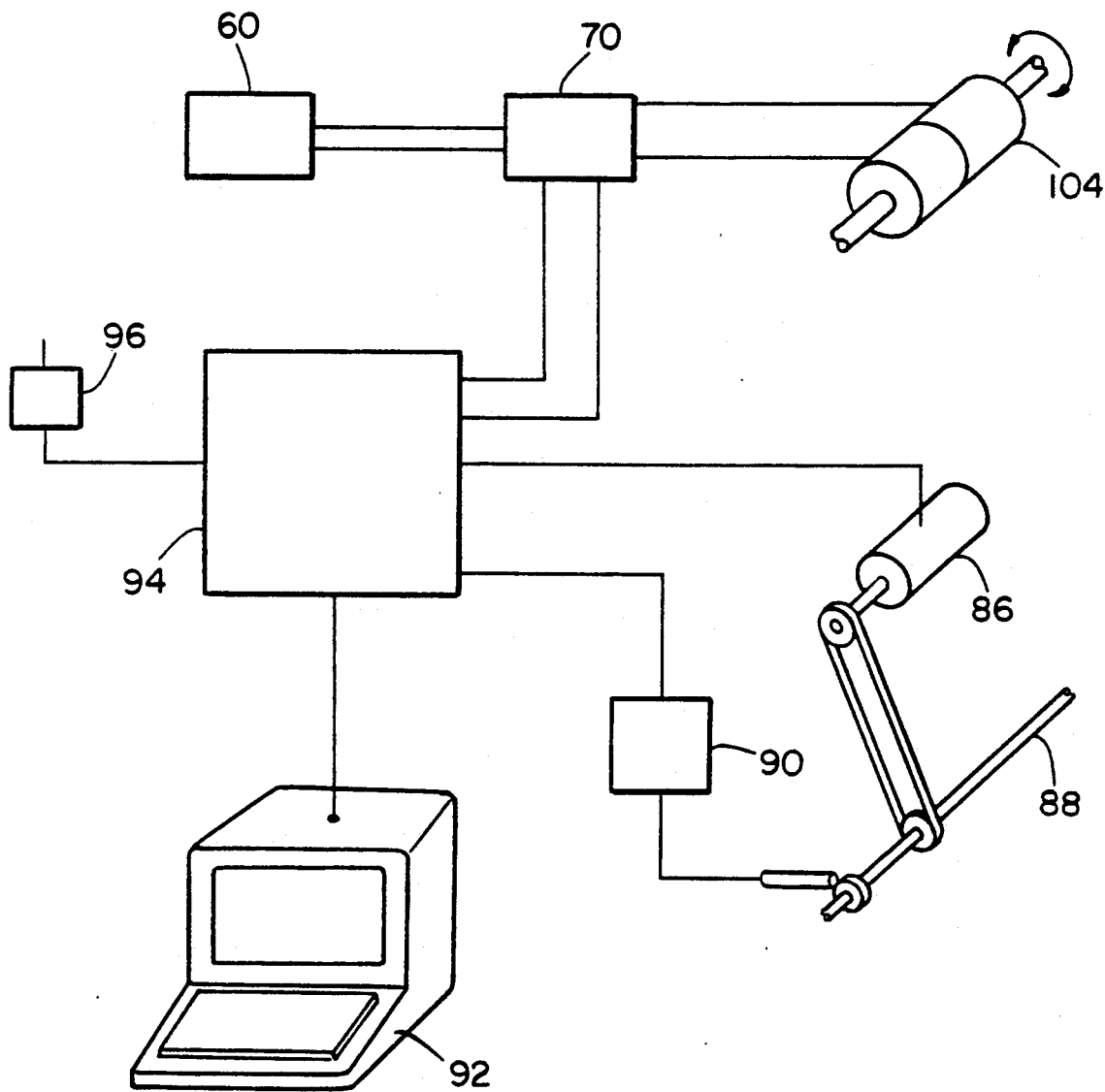
FIG. 3 shows a schematic representation of a phasing control system employed in the present invention.

Referring again to FIG. 2, the shown embodiment of the invention includes a transferring means comprising a separating means, such as blade member 72, for selectively guiding a predetermined, metered quantity 64 of the particulate material from accumulation region 22 into receiving chamber 62. The receiving chamber gathers and temporarily holds the particles, and a suitable gas supplying means 58 provides at least a portion of a delivery gas stream 26 to move the selected quantity of particulate material 64 from receiving chamber 62 into delivery conduit 30. A controlling means, such as an electromechanical relay or an electronic, solid-state relay 66, selectively operates and regulates gas supplying means 58 to provide an initial delivery gas stream **26*a* which entrains and intermittently propels particulate quantity 64 into delivery conduit 30** in a sequentially pulsed manner.

The embodiment of the invention illustrated in FIG. 2 can advantageously provide a distinctive, improved pulsing system for supplying the regulated, metered quantities of superabsorbent particles. The shown embodiment of the pulsing system can be conceptualized as working in two stages. First it employs a segregating means to separate and collect, then it employs a transferring means to release and deliver.

In the illustrated embodiment of the separating and collecting operations, a substantially continuous conveying stream composed of a mixture of superabsorbent particles and gas (air) enters inlet section 52 of curved conduit 48. The particles/air mixture flows around the curved conduit, and the relatively greater momentum and inertia ("centrifugal force") of the particles causes the more dense particulate material to gather along and hug the radially outward wall 50 of the conduit pipe. This operation creates a stratified mixture within conduit 48 within which the flowing particles are concentrated in accumulation region 22 of the conduit. When the stratified mixture reaches separating blade 72, nearly all of the particulate material is flowing along outer wall 50. As a result, a major portion 78 of the conveying air flows over the top of the separating blade. Concurrently, the moving stream of superabsorbent particles and a minor portion 79 of the conveying air are directed into receiving chamber 62. A wire mesh screen 74 is located at one end of receiving chamber 62 and the movement of the particle stream is directed against the screen to stop and collect the superabsorbent particles. The size of the screen mesh is sufficiently small to substantially prevent the passage of superabsorbent particles therethrough. As a result, the particles are operably collected within chamber 62, and further segregated from the conveying air stream as the minor portion of conveying air 79 operably deflects away from the collected particles and departs from chamber 62 through exit opening 76.

To release and deliver the particles, flow regulating means such as control valve 68 can be triggered at a selected time to deliver a regulated, timed burst of initial delivery air **26*a*, which is directed through screen 74 from a suitable gas supplying means 58. The air blast pushes the collected superabsorbent particles through receiving chamber 62 and out an open, exit end 76** of the receiving chamber.

In an alternative configuration of the invention, the release and delivery of the particles may optionally be accomplished with a piston-type mechanism. The piston can be selectively actuated with a conventional drive mechanism, such as a pneumatic actuator, a mechanical cam mechanism or a driven linkage actuated by an electromechanical servo, to operably push or otherwise force the collected quantity of superabsorbent particles back into the minor portion 79 of the conveying airstream. Conveying air portion 79 can then entrain the particles and carry them out the exit end of the receiving chamber into delivery air stream 26.

Meanwhile, the major portion 78 of conveying air stream 46, which portion was initially separated from the superabsorbent particles, continuously flows through recirculation conduit 80 and is directed to flow through a generally annular region which is circumferentially adjacent to at least a portion of the outside of receiving chamber 62. As a result, this air stream is effectively converted and reconfigured to become a delivery gas stream portion **26*b*, which flows past chamber 62 and then away from the chamber through outlet conduit 82. As gas stream portion 26*b* flows past chamber 62, the gas stream combines with the residual conveying air portion 79 departing the chamber. Each pulse of superabsorbent particles departing from receiving chamber 62 is conveyed through outlet 82 into delivery conduit 30, and during this operation, the air/particle pulse merges into and flows along with gas stream portion 26*b***.

The resultant, combined delivery air stream 26 moving through conduit 30 includes a series of intermittent, spaced-apart pulse regions each of which comprises a mixture of air and superabsorbent particles. Interposed between the spaced-apart, pulse regions are air stream buffer regions which contain lesser amounts of particles and, preferably, are substantially free of superabsorbent particles. As the pulse regions move through delivery nozzle 36 (FIG. 1), the particle/air pulses can be selectively shaped and released into forming chamber 32. The particles within the pulse have a relatively high velocity, for example, about 3000 feet/minute (about 15 meters/sec), and the momentum of the particles carries the particles from nozzle 36 to traverse particular, predictable distances through forming chamber 32 to deposit into the selected substrate, such as a fibrous web.

Various types of conventional control valves and control relays may be employed with the present invention. In the illustrated embodiment, solenoid control valve 68 may be a 56C-61-1-CA valve manufactured by MAC Valves, Inc. located in Wixom, Mich. The control relay 66 may be a solid-state relay, such as an ODC5 relay manufactured by OPTO 22, a business located in Huntington Beach, Calif.

Gas supplying means 58 delivers air at a pressure of not more than about 30 psi (about 207 kPa), and preferably delivers air at a pressure of not more than about 20 psi (about 138 kPa). The corresponding peak velocity of the delivered air is about 9000 ft/min (about 46 m/sec). In addition, gas supplying means 58 can be configured to deliver air at a pressure of not less than about 1 psi (about 7 kPa), and preferably at a pressure of not less than about 3 psi (about 21 kPa) to provide improved effectiveness. The corresponding peak velocity of the delivered air is about 1000 ft/min (about 5 m/sec). In the shown embodiment, gas supplying means 58 delivers clean, dry, compressed air at a pressure of about 6 psi (about 41 kPa) with a peak air velocity of about 3000 ft/min (about 15 m/sec).

To properly control and sequence the desired placement of particulate quantities 64 within fibrous web 42

(FIG. 1), an aspect of the invention includes a phasing means for sequencing the operation of transferring means 24 to provide a desired registration between particulate quantity 64 and a selected deposition region along a machine direction of fibrous web 42. A particular embodiment of the invention includes the phasing control system representatively shown in FIG. 3. The primary system for determining machine position and timing can, for example, incorporate a conventional line shaft encoder 86, which is operably connected to the primary line shaft 88 of the apparatus. In addition, a reference signal generator 90 is operably connected to line shaft 88 to generate one reference pulse per each individual product section, which is intended to be derived from fibrous web 42. The output from reference generator 90 and line shaft encoder 86 are directed to a programmable controller, such as a computer, through suitable signal conduits. A conventional input device, such as a keyboard system 92, is employed to set variable control parameters in computer 94. The computer in turn, selectively triggers appropriate devices, such as solid-state relays 70, to activate selected components, such as valves and actuators 104. A suitable power supply, such as electrical power supply 60, provides the energy needed to operate the system.

In the shown embodiment, line shaft encoder 86 may be a 63-P-MEF-2000-T-0-00GH device manufactured by Dynapar Corp. located in Gurnee, Ill. The encoder may, for example, be configured to generate 2000 pulses per revolution.

Reference signal generator 90 may, for example, comprise a B15-G18-ANGX proximity switch manufactured by TURCH, a business located in Minneapolis, Minn. A suitable computer may, for example, comprise a device manufactured and designated as a PME 68-23 CPU by Radstone Technology, a company located in Pearl River, N.Y.

In the illustrated embodiment, the pulser mechanism can be operably controlled by employing a reference signal generated at a predetermined time and position along the apparatus. For example, the reference signal may be generated at a reference point corresponding to a machine position at which portions of fibrous web 42 are cut away to form the leg openings of a disposable diaper. Accordingly, computer 94 can be programmed to trigger an actuator, such as solenoid valve 68 (FIG. 2), at the appropriate number of encoder counts after the generation of the "leg cutout" reference signal. Alternatively, the chosen reference point may be the "fluff cutoff" reference signal, the machine position and operation at which fibrous web 42 is separated into individual, end-product sections.

To properly locate the particle quantity 64 along the machine direction of fibrous web 42, several other parameters should also be taken into account. One parameter is the transport delay parameter, which corresponds to the time period between triggering the control valve 68 and the arrival of the particulate quantities 64 at the foraminous forming layer 38 within the web forming chamber. The exact value of this parameter can be readily determined by persons skilled in the art, and will depend upon factors such as the specific dimensions of the apparatus, operating speed of the apparatus, and speed of the moving particles.

A second parameter is the dwell time which corresponds to the time period over which solenoid valve 68 remains energized. Another, optional parameter is the "second-pulse offset" parameter which corresponds to the delay, in encoder counts, between discrete pulses of particles when multiple quantities 64 are to be delivered into an appointed end-product section of fibrous web 42. Such multiple quantities may be provided by a multi-function, single unit transferring means, or by a multiple unit transferring means. The reference to the end-product section of the web is a reference to the fact that web 42 may, for example, eventually be separated into individual absorbent bodies or pads for use in disposable diapers. Each particular machine-direction length of web 42, which corresponds to an individual pad, could then be identified as an end-product section of the web.

A detecting means 96, such as a fiber optic photo-eye sensor, can be positioned in operable proximity to delivery nozzle 36 to ascertain the absence or presence of the individual, pulsed quantities 64. Alternatively, detecting means 96 may comprise a sensor which operates on the basis of the tribo-electric effect. For example, the sensor may be a Model 2603 Triboflow sensor available from Auburn International, Inc. located in Danvers, Mass. End-product sections of fibrous web 42 which do not receive an appropriate quantity of particles can be automatically culled from the apparatus.

Figure 4:
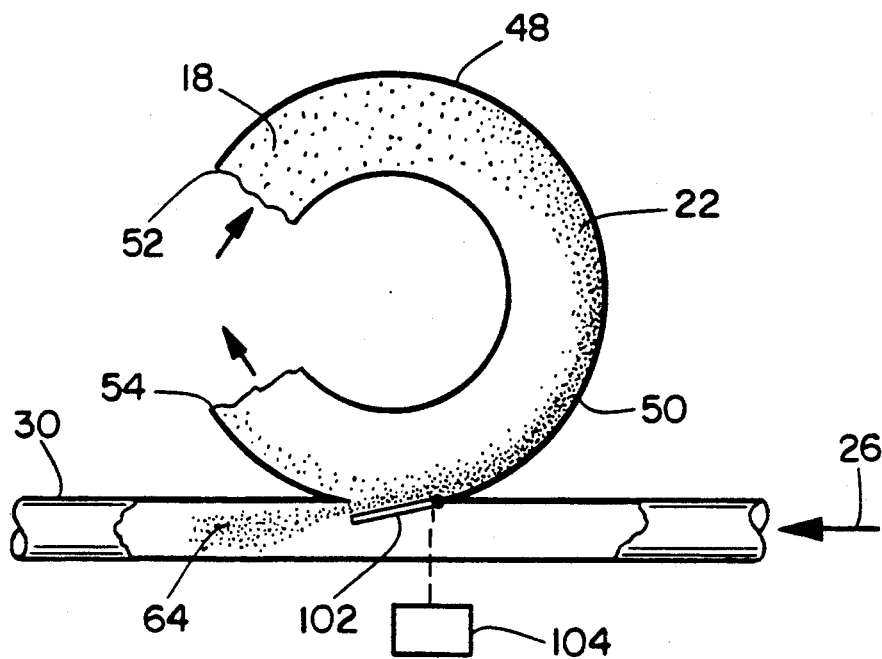
FIGS. 4 and 4A representatively show an embodiment of the invention which includes a diverter mechanism for producing intermittent flow.
Figure 4A:
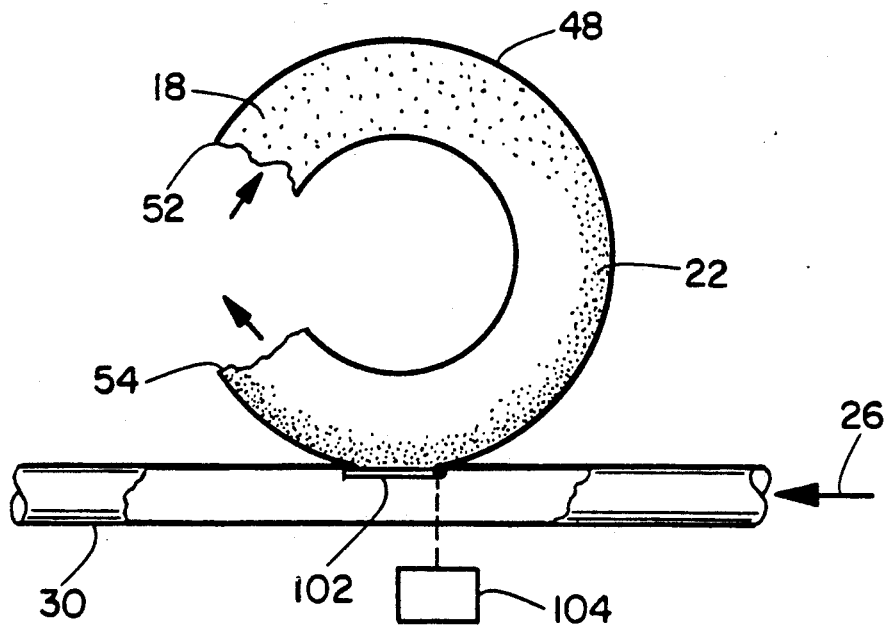

In an aspect of the invention representatively shown in FIGS. 4 and 4A, transferring means 24 (FIG. 1) can comprise a diverter system. With regard to the illustrated embodiment of the diverter system, supply stream 18, which contains the mixture of gas and superabsorbent particles, enters curved conduit 48 through inlet section 52, and the particles become segregated in accumulation region 22 along the radially outward wall of the conduit. At a selected position along the curved path of conduit 48, delivery conduit 30 is connected in operable communication therewith. The shown embodiment, for example, includes a delivery conduit 30 which is positioned generally tangential to curved conduit 48. A gas supplying means provides a delivery air stream 26 through delivery conduit 30, and a diverter regulator member, such as flap member 102 is positioned at the point of intercommunication between curved conduit 48 and delivery conduit 30. Regulator flap 102 is selectively moveable between a closed position (FIG. 4A) and an open position (FIG. 4) by the operation of a suitable diverter actuator 104. When regulator flap 102 is in its closed position, supply stream 18 is recirculated out of conduit 48 through outlet section 54.

When regulator flap 102 is in its open position, a metered quantity of superabsorbent particles 64 can be allowed to pass from curved conduit 48 into delivery conduit 30. Delivery airstream 26 can then transport the pulsed quantity of particles to delivery nozzle 36 and forming chamber 32. As previously discussed, a phasing means is employed to selectively sequence the operation of diverter actuator 104 and regulator flap 102 to provide a desired registration between particle quantity 64 and selected deposition regions along the machine direction of web 42 (FIG. 1). In particular, computer 94 (FIG. 3) is appropriately programmed to trigger the operation of regulator flap 102 to deliver one or more pulse quantities of particulate material into each appointed end-product section of fibrous web 42.

Particular aspects of the invention may be distinctively configured to provide a plurality of different open positions for regulator flap 102. The regulator flap may be moveable to two or more selected, "open" positions, each of which is arranged to deliver a different flow rate of particulate material into delivery conduit 30. For example, regulator flap 102 may be advantageously coupled to a servo drive system which is programmable to incrementally move the regulator flap to a plurality of different flap positions in accordance with a predetermined sequence. As a result, the invention can be constructed and arranged to provide a selectively "shaped" distribution pattern of particulate material within each individual, end-product section of web 42. The sequential, incremental movements of regulator flap 102 may, for example, be actuated by a servo drive mechanism which is operably coupled to a programmable control system, such as a computer, in a manner well known in the art.

In the shown embodiment, regulator flap 102 rotates about a pivot which is located at an "upstream" section of the flap, with the regulator flap extending generally downstream from the pivot. During operation, the flap moves to "open" positions at which the flap protrudes into delivery conduit 30. The pivot may alternatively be located at a downstream section of regulator flap with the flap extending generally upstream from the pivot. With such a configuration, regulator flap 102 can be arranged and structured to move to "open" positions at which the flap protrudes into curved conduit 48.

Figure 5:
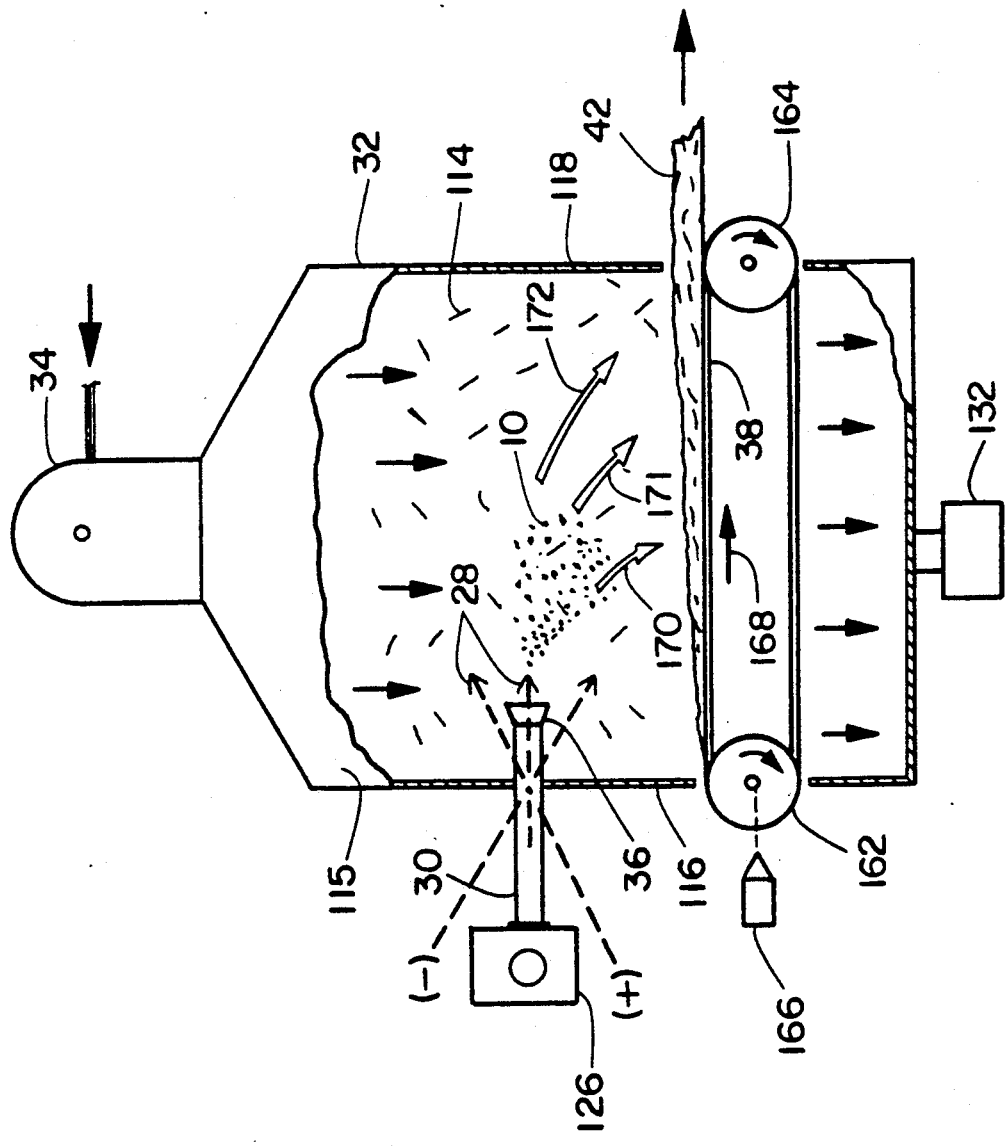
FIG. 5 representatively shows a forming chamber employed with the present invention.

FIG. 5 provides a more detailed illustration of web forming chamber 32. The chamber includes a fiber delivery means, such as fiberizer hammermill 34, which provides a flow of fibrous material 114 within the forming chamber. Foraminous forming layer 38, which is located in forming chamber 32 and movable therein, is configured to receive a deposit of fibrous material 114 thereon. Piping means such as delivery conduit 30 and one or more nozzles 36, supply a flow of dispersed bodies of high absorbency material, such as superabsorbent polymer particles 10. This flow of particles enters forming chambers 32 and intermixes with the flow of fibrous material 114 therein. Regulating means, such as flow angle adjuster 126, controls a flow velocity 28 of particulate material 10 within the fibrous material 114 deposited onto forming layer 38 to form fibrous web 42.

Forming chamber 32 includes side walls 115 and end walls which are constructed and arranged to define a generally enclosed volume. End walls 116 and 118 have suitable entrance and exit openings formed therethrough to allow the entry of forming layer 38 and the removal of airlayed fibrous web 42 from the forming chamber.

Hammermill 34 may comprise any one of a number of types of conventional fiberizing devices. Sheets of selected fibrous material are typically fed into the hammermill, and are disintegrated into a plurality of individual fibers 114 which are injected or otherwise introduced into chamber 32. Fibers 114 are typically composed of absorbent, woodpulp fibers commonly referred to as fluff. The fibers may also be composed of staple fibers, polymeric fibers, cellulosic fibers and mixtures thereof, as well as mixtures of absorbent fibers with generally hydrophobic fibers. The fibrous material may optionally be treated to impart desired levels of hydrophilicity, employing techniques well known in the art.

The forming apparatus of the invention may further include vacuum means 132, such as a conventional blower mechanism, for creating a selected pressure differential through forming chamber 32 and past forming layer 38. The vacuum means is typically located underneath forming layer 38 to create an air flow through chamber 32 which is generally directed from hammermill 34 and past forming layer 38. This airflow helps to direct and control the deposit of fibers 114 and particles 10 onto the forming layer.

Forming layer 38, for example, may comprise a foraminous forming screen configured as an endless belt which moves about support rollers 162 and 164. A suitable driving means, such as electric motor 166, is operably connected to move forming layer 38 through chamber 32 at a selected speed along machine direction 168. Fibers 114 and particles 10 deposit onto the portion of forming layer 38 within forming chamber 32 to form fibrous web 42, which eventually develops into an absorbent body 240 within an absorbent article. Since forming layer 38 moves generally from end wall 116 toward the exit opening through end wall 118, the depth or thickness of web 42 on any particular section of forming layer 38 gradually increases as that forming layer section traverses through the forming chamber. The fiber deposition rate onto forming layer 38 and the movement speed of the forming layer can be suitably adjusted to control the finally formed thickness of the airlayed fibrous web 42.

Figure 6:
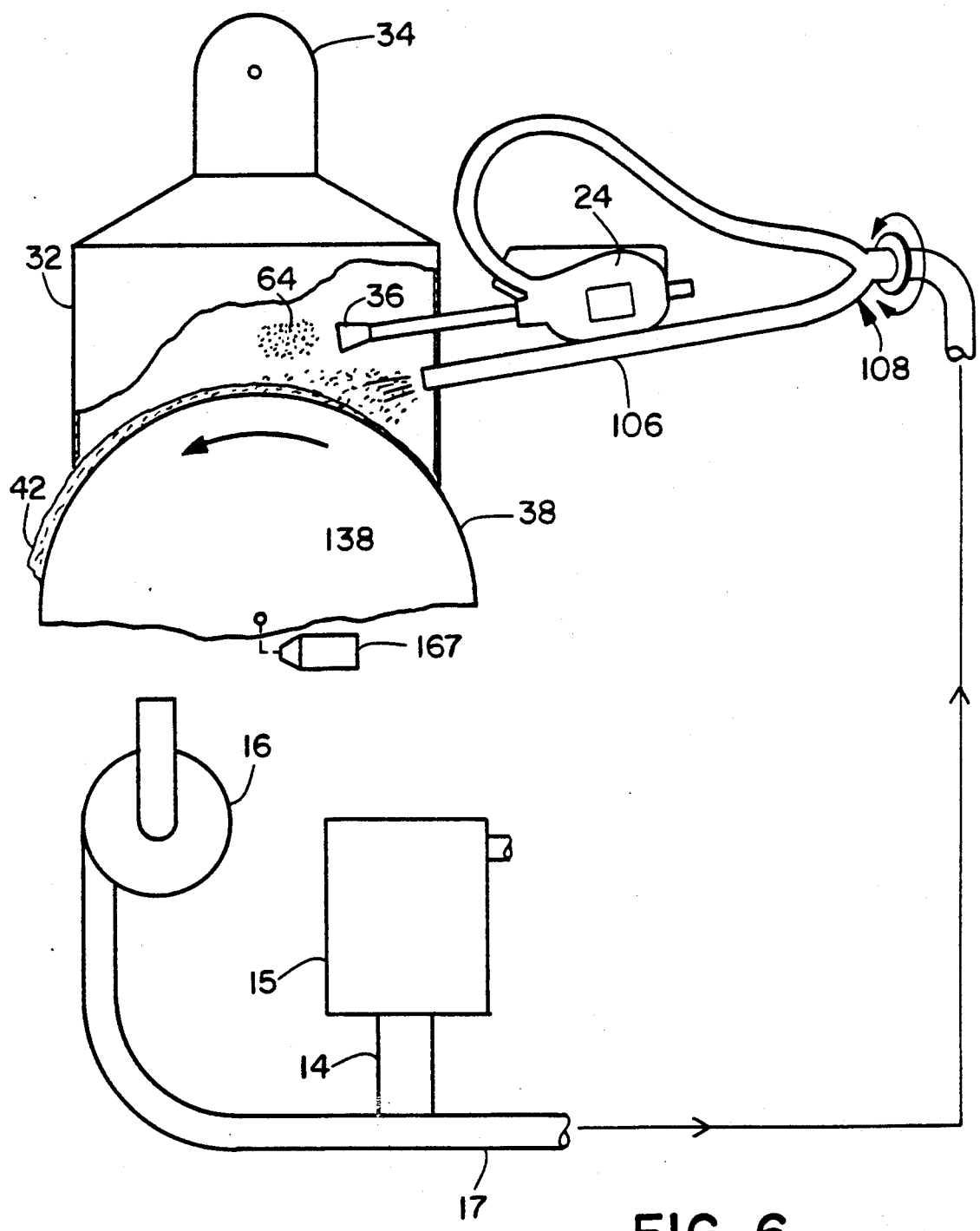
FIG. 6 representatively shows an embodiment of the invention which includes a combination of mechanisms for producing different flows of particulate material.

In another aspect of the invention, forming layer 38 comprises a foraminous forming screen carrier on an outer circumferential surface of a rotatable drum 138, as representatively shown in FIG. 6. A suitable driving means, such as motor 167, rotates drum 138 to move forming layer 38 through forming chamber 32.

The invention may include single or multiple nozzles 36 which, for example, may comprise a conduit of circular cross-section measuring about 5 centimeters in diameter. If desired, other regular or irregular nozzle shapes or sizes may be employed.

Referring again to FIG. 5, the nozzles may protrude into chamber 32 a predetermined distance to adjust the distribution of particulate material through the thickness of web 42. A larger amount of protrusion can, for example, reduce the amount of particles deposited near the forming layer side of web 42.

Depending on the size and mass of the individual particles, the dispersed particles will tend to follow various trajectories 170–172 to intermix with the flow of fibers 114 moving through chamber 32 toward forming layer 38. Some of the particles will follow a shorter trajectory 170 to deposit superabsorbent particles into web 42 at locations nearer end wall 116. Other particles will follow longer trajectories 172 to deposit into web 42 at locations closer to end wall 118. The remainder of particles will follow intermediate trajectories 171 to deposit into web 42 at more centrally located, intermediate regions between end walls 116 and 118. Since web 42 is gradually increasing in thickness as it traverses through chamber 32, particles 10 can be selectively distributed through the thickness dimension of web 42 to produce a desired concentration gradient therein.

To produce desired distribution patterns and gradients through the web thickness, an initial flow velocity 128 of the air/particle stream moving into chamber 32 can be selectively regulated by adjusting the angular direction of the flow, the height of the nozzles above forming layer 38, and the speed of the flow. Flow regulating means comprising blower control 158 in the shown embodiment (FIG. 1) adjusts the volume rate of gas flow into the system, and as a result, can adjust the magnitude of the mean velocity or speed of the gas/particle flow. For example in one embodiment of the invention, blower 28 is adjusted to provide a mean flow velocity of the air/particle mixture which measures at least about 5 meters/seconds. If the flow velocity is increased, relatively more particulate material can be deposited toward the upper free surface of web 42. If the flow velocity is decreased, relatively move particulate material can be deposited toward the forming layer side of web 42. In a particular aspect of the invention, the flow velocity of the air/particle mixture is within the range of about 5-45 meter/seconds.

The geometry and size of delivery nozzles 36 may be adjusted to control the distribution of particles along the cross-direction of the apparatus. In addition, the initial direction of the air/particle flow into chamber 32 can be selectively changed employing angle adjusting mechanism 126, which is operated to change the angular orientation of nozzle 36 with respect to the local horizontal direction. In a particular aspect of the invention, angle adjusting mechanism 126 comprises a rotatable connection located within delivery conduit 30. It should be readily apparent that angle adjusting mechanism 126 should be configured with a structure which does not substantially interfere with any intermittent, pulsed quantities of particles being transported through the delivery conduit.

Delivery nozzles 36 can be suitably adjusted to a nonparallel angle slanted toward or away from forming layer 38. If the nozzle is angled toward the forming layer, relatively more particulate material can be deposited near the forming layer side of web 42. If the nozzle is angled away from forming layer 38, relatively more particulate material can be deposited near the upper, free surface side of web 42. For example, in a particular aspect of the invention, nozzle 36 is constructed and arranged to be pivotable within a range of approximately plus (upwardly) 45° to minus (downwardly) 60°, relative to a plane positioned generally parallel to the forming layer. Preferably, the nozzle is pivotable within the range of about plus 10° and minus 45° relative to such plane, respectively away or toward the forming layer.

The entry angle of the moving superabsorbent particles can be adjusted by selectively orienting nozzle 36, and velocities of the particles can be appropriately regulated to impart desired, predetermined trajectories to the particles. As a result, particular particles can travel different horizontal distances through chamber 32 in a direction generally parallel to the machine direction of the apparatus. In the illustrated embodiment the particles move along with the movement of the formed fibrous web, but in alternative embodiments, the apparatus can be configured to move the particles counter to the movement of the fibrous web. The difference in horizontal distances can cause differing amounts and/or differing weight percent concentrations of the particles to be selectively placed at various desired levels through the thickness dimension of the fibrous web.

Particular aspects of the invention can include combinations of the various, different types systems for delivering particulate material into forming chamber 32. As representatively shown in FIG. 6, for example, the invention may be configured to include a pulser-type transferring means 24 in combination with a continuous delivery system 106. The pulser-type device injects discrete, selected quantities of superabsorbent particles into fibrous web 42, and continuous delivery system 106 provides a substantially continuous mass flow rate of superabsorbent particles into the forming chamber for incorporation into the fibrous web.

Figure 13:
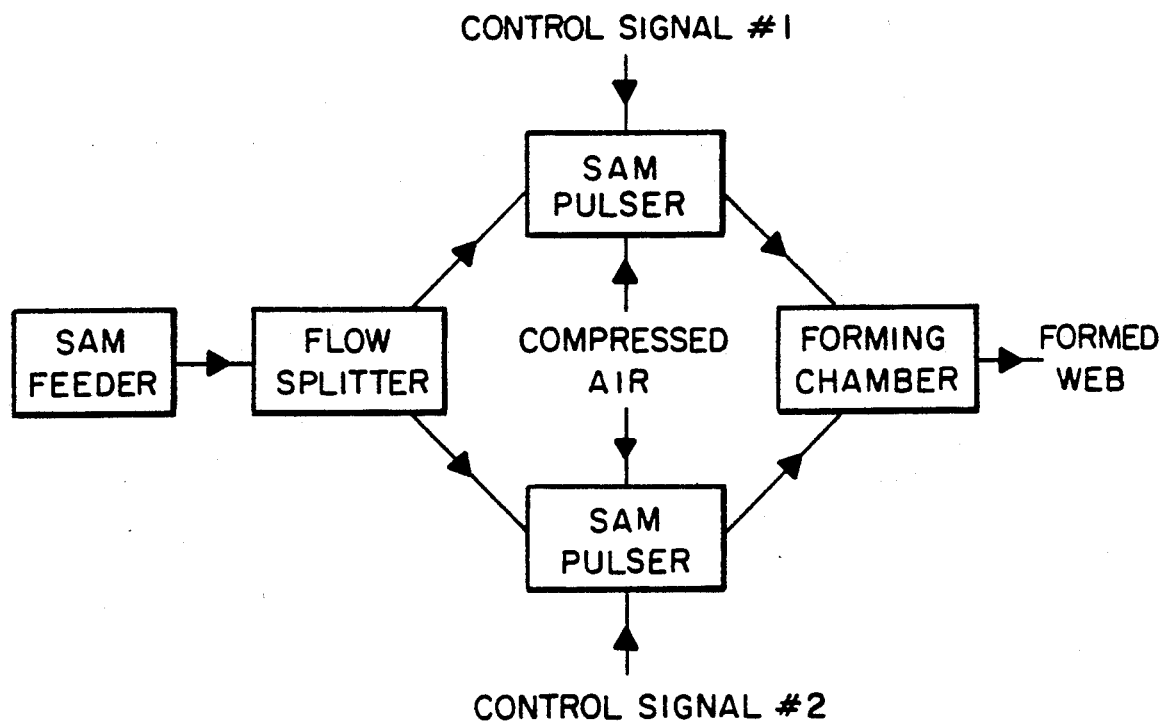
FIGS. 13 and 13A show a schematic block diagram of an apparatus comprising two pulser-type systems, and a graphic representation of the distribution of particulate material produced along the longitudinal dimension of the fibrous web by such an apparatus, respectively.
Figure 13A:
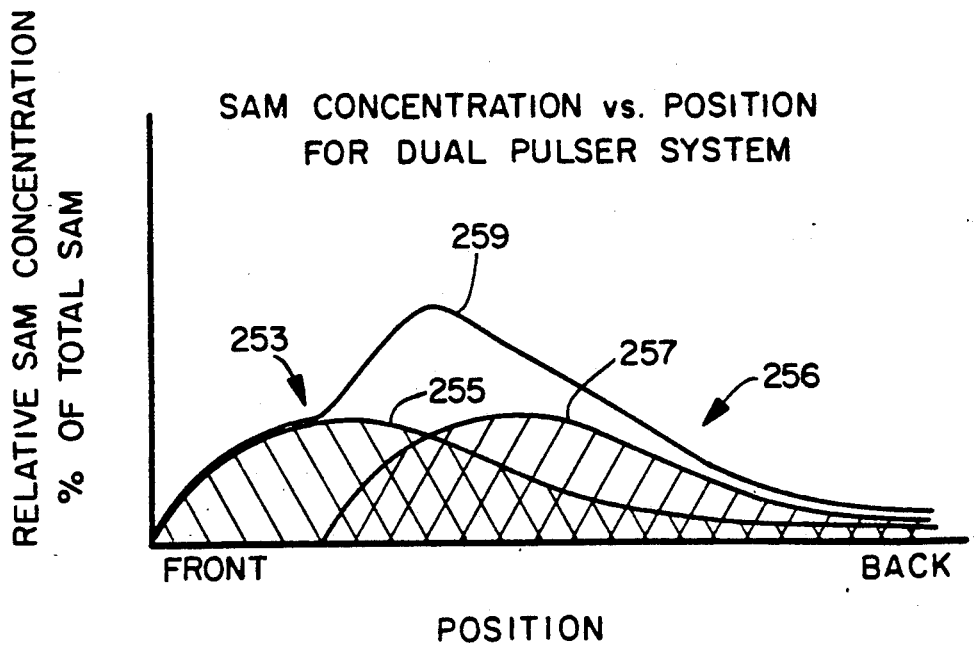
Figure 14:
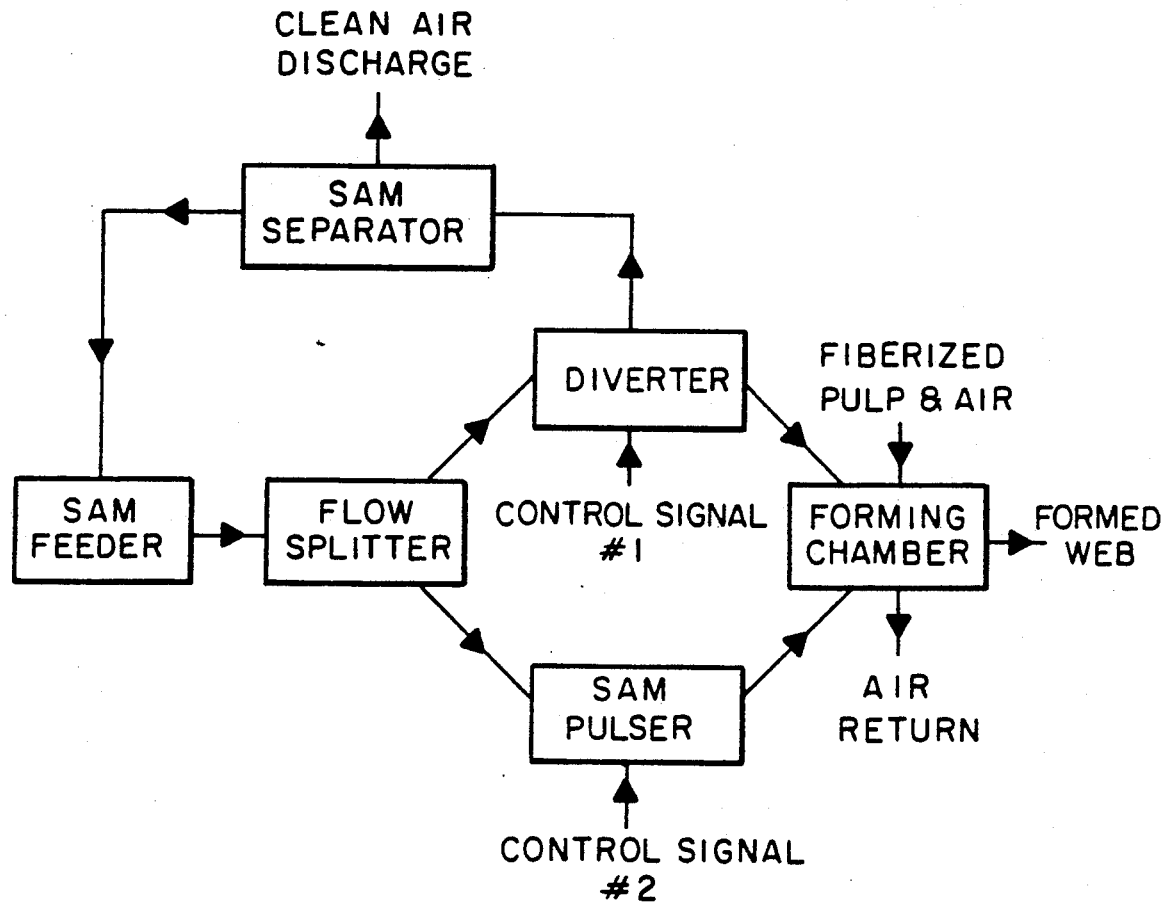
FIGS. 14 and 14A show a schematic block diagram of an apparatus comprising a pulser-type system and a diverter-type system, and a graphic representation of the distribution of particulate material produced along the longitudinal dimension of the fibrous web by such an apparatus, respectively.
Figure 14A:
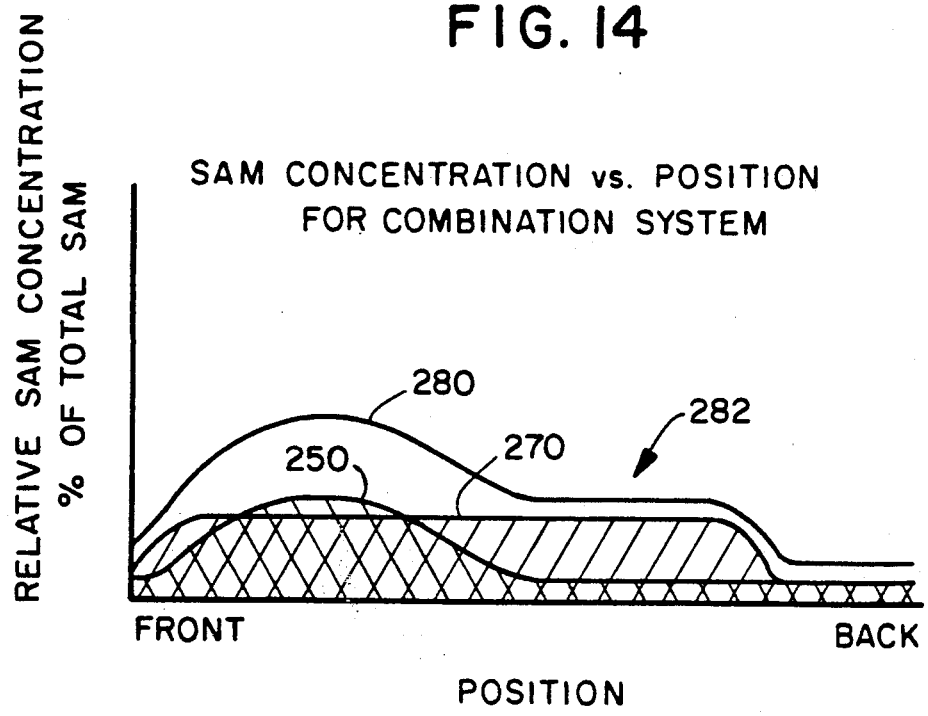

As further examples of combinations of delivery systems, FIGS. 13 and 13A show a schematic representation of an embodiment of the invention wherein the transferring means includes two pulser-type systems, and FIGS. 14 and 14A show a schematic representation of an embodiment wherein the transferring means includes a pulser-type system and a diverter-type system.

Figure 8:
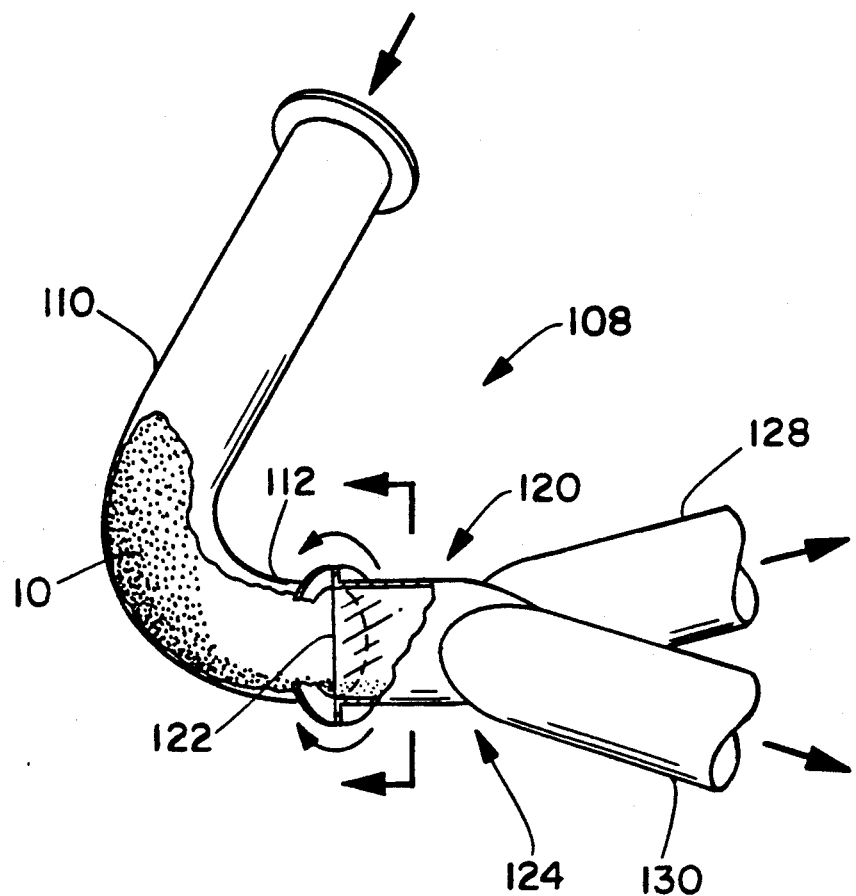
FIGS. 8 and 8A representatively show a metered, flow splitting mechanism.
Figure 8A:
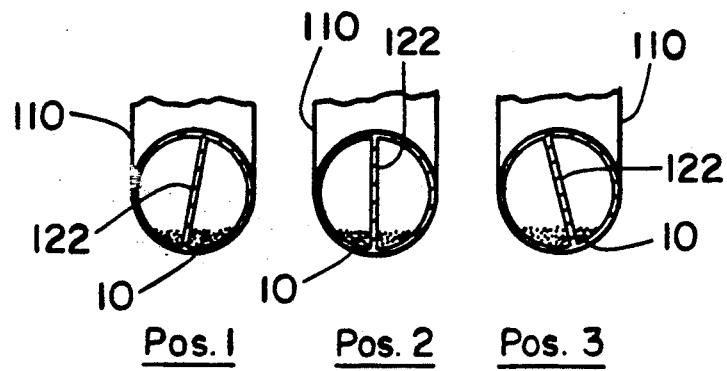

To support the operation of multiple transferring systems and delivery systems, a flow splitting means 108, representatively shown in FIG. 8, can be employed to partition the particle/air supply stream into separate streams. Flow splitter 108 includes an isolating means such as curved pipe 110, to locate particles 10 in a predictable region within the curved pipe. As previously discussed in the context of segregating means 20, the movement of particles through pipe 110 along a curved arc concentrates the particles toward the radially outward wall of the pipe. As a result, at the pipe outlet 112, most of the particles are flowing along the outside wall, and the particles are directed into a dividing mechanism 120. The dividing mechanism connects to pipe outlet 112 and is circumferentially rotatable with respect to the pipe outlet. The inlet region of the dividing mechanism is substantially circular in cross-section and includes a knife member 122 located along a diameter thereof. The two major surfaces of the knife member extend axially along the length of the dividing mechanism. As illustrated in FIG. 8A, knife member 122 is aligned generally along the radius of curvature of the curved path defined by pipe 110, and extends along the radial and circumferential directions of the pipe. As a result, knife member 122 can cut the particle stream into two portions, which are directed toward an outlet section of dividing mechanism 120. In the illustrated embodiment, outlet section 124 branches off into a Y-configuration. A first particle stream is directed into a first divider arm 128 and a second particle stream is directed into a second divider arm 130. The relative proportion of particles directed into divider arms 128 and 130 will depend upon the particular rotational position of knife member 122. Accordingly, the rotational position of knife member 122 can be selectively adjusted to direct equal or different proportional amounts of superabsorbent particles into each of the divider arms. For example, three possible rotational positions of the knife member are illustrated in FIG. 8A.

In yet another aspect of the invention, the method and apparatus may include multiple transferring systems configured to deliver two or more different types of particulate materials into the substrate. For example, one transferring mechanism may deliver particles of superabsorbent material and a second transferring mechanism may deliver particles of a non-superabsorbent material. As another example, each of the transferring systems may be constructed and arranged to deliver a distinctively different type of superabsorbent material. Each type of superabsorbent could have a particular set of performance characteristics, and each type of superabsorbent could be selectively placed at predetermined positions within the substrate to provide an advantageous combination of absorbency characteristics.

Figure 9:
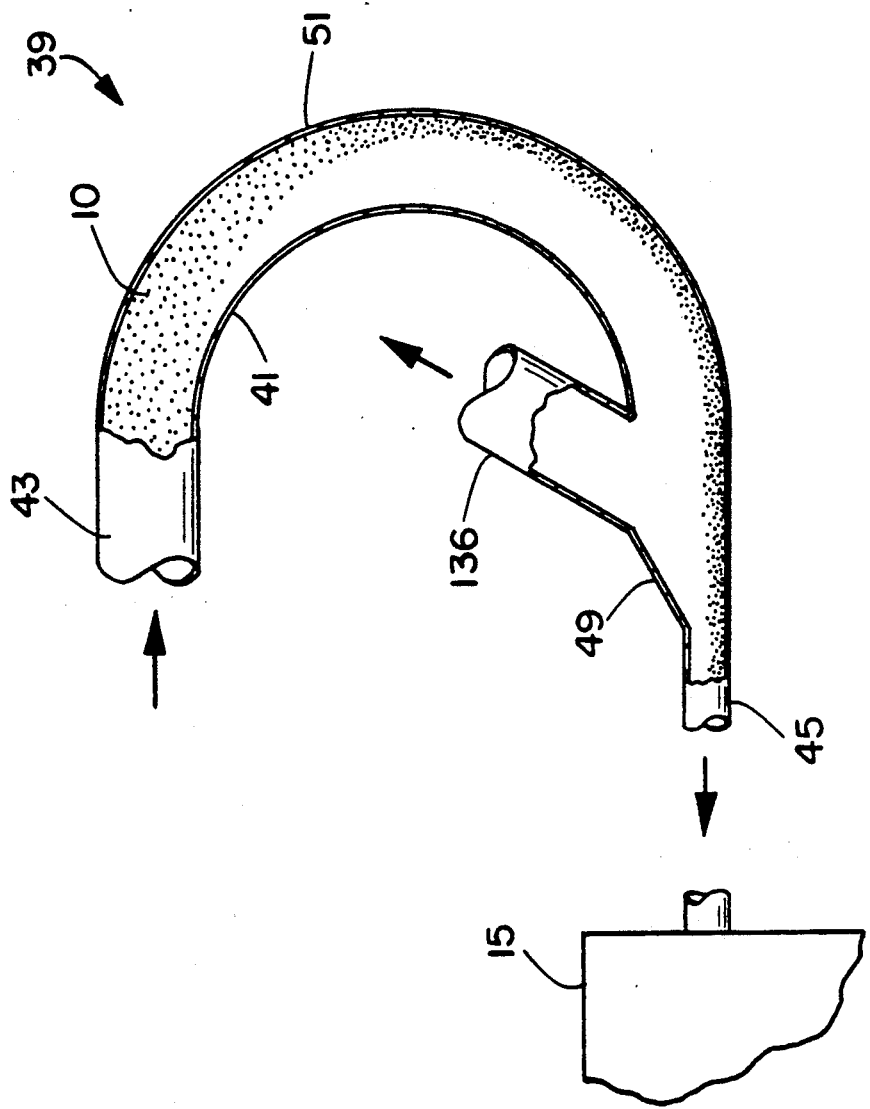
FIG. 9 representatively shows a particle recovery system employed with the present invention.

A representative particle recovery system 39 is shown in more detail in FIG. 9. In the illustrated embodiment, the recovery system comprises a curved conduit 41 which includes an inlet section 43, an outlet section 45 and an exhaust conduit 136. The moving, incoming gas/particulate mixture enters inlet section 43, and as the mixture moves along the arcuate path defined by the curved conduit, particles 10 become segregated towards the radially outward wall 51. Outlet section 45 is located at a radially outward portion of curved conduit 41 and is connected in operable communication with a particle reservoir section 15 of feeder mechanism 14 (FIG. 1). As a result, particles 10 can be directed through the outlet section and toward the reservoir section. An exhaust conduit 136 is connected to outlet section 45, and the remaining gas stream is directed into exhaust conduit 136 by deflector member 49 and by a pressuring means which provides a selected pressure differential between the gas pressure within conduit 41 and the gas pressure within reservoir 15. In particular, the reservoir static gas pressure is greater than the conduit gas pressure. As a result, the relatively high momentum of the moving particles can operably carry the particulate material through the static pressure differential and into reservoir 15. The gas pressure differential, however, substantially blocks the gas portion of the gas/particulate mixture from moving into the reservoir. The gas portion is instead operably deflected and redirected to move through exhaust conduit 136. The deflected gas stream is substantially free of particulate material and may optionally be recirculated through appropriate conduits to provide at least a portion of delivery gas stream 26 (FIG. 1), as desired. Thus, the particulate material can be efficiently separated from its associated transporting stream of gas and advantageously recycled for use into reservoir 15. The particle recovery system of the invention can advantageously recover more than 90% of the particles from the incoming gas/particle mixture. Particular embodiments of the recovery system can recover about 95% of the particles from the incoming gas/particle mixture.

Figure 10:
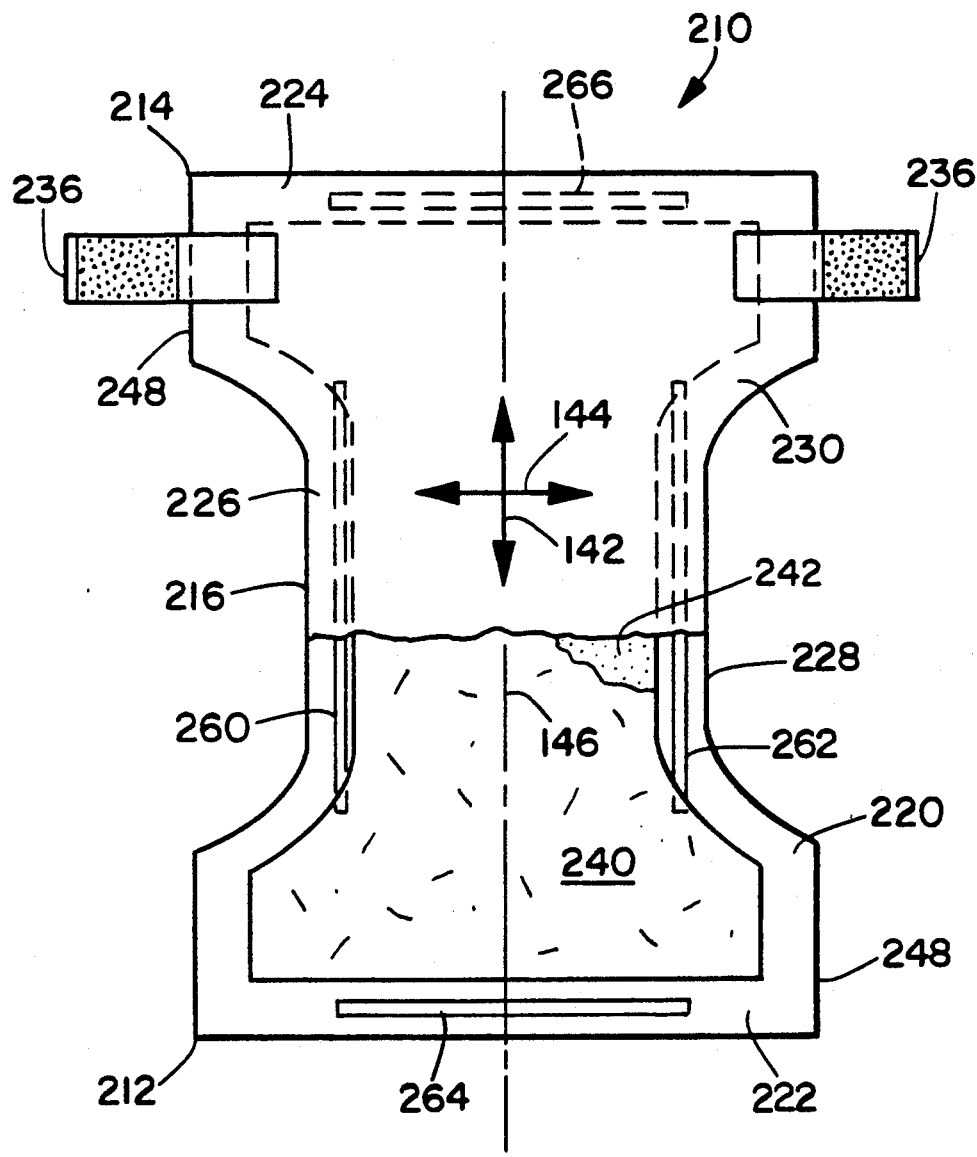
FIG. 10 representatively shows an absorbent diaper-type article which incorporates an absorbent body of the present invention.

With reference to FIG. 10, an integral absorbent garment article, such as disposable diaper 210, generally delimits a front waistband panel-section 212, a rear waistband panel-section 214, and an intermediate section 216 which interconnects the front and rear waistband sections. The absorbent article comprises a substantially fluid impermeable backsheet layer 220, a liquid permeable topsheet layer 230 positioned in facing relation with backsheet layer 220, and an absorbent body 240 is located between the backsheet layer and topsheet layer. For reference purposes, the diaper has a longitudinal direction 142, a cross-direction 144 and a longitudinal centerline 146.

Marginal portions of diaper 210, such as marginal sections of backsheet 220, may extend past the terminal edges of absorbent body 240. In the illustrated embodiment, for example, backsheet 220 extends outwardly beyond the terminal marginal edges of absorbent body 240 to form garment side margins 226 and 228 and garment end margins 222 and 224. Topsheet 230 is generally coextensive with backsheet 220, but may optionally cover an area which is larger or smaller than the area of backsheet 220, as desired.

Diaper 210 may be of various suitable shapes. For example, the diaper may have an overall rectangular shape, T-shape or an approximately hour-glass shape. In the shown embodiment, diaper 210 has a generally I-shape.

The various components of diaper 210 are integrally assembled together employing various types of suitable attachment means, such as adhesive, sonic bonds, thermal bonds, and the like, and combinations thereof. In the shown embodiment, for example, topsheet 230 and backsheet 220 are assembled to each other and to absorbent body 240 with lines and patterns of adhesive, such as a hot melt, pressure-sensitive adhesive. Similarly, other diaper components, such as elastic members 260 and 264 and fastening members 236, may be assembled into the diaper article by employing the above-identified attachment mechanisms.

The illustrated embodiment of diaper 210 includes ear portions 248, which extend laterally along the diaper cross-direction 144 and are positioned at least at one waistband section of diaper 210, preferably at the rear waistband section 214. Ear portions 248 may also be located at front waistband section 212 of the diaper. The ear portions may be integral with backsheet layer 220, or may comprise separate sections, which are composed of the same or different material than backsheet 220 and are suitably assembled and attached to the backsheet layer. Ear sections 248 typically provide extensions of the diaper waistband suitable for completely encircling the waist of the wearer during use.

Fastening means, such as adhesive tapes 236, are employed to secure the diaper on a wearer. Alternatively, other fastening means, such as buttons, pins, snaps, hook-and-loop fasteners, mushroom-and-loop fasteners, or the like, may be employed.

To provide improved fit and to help reduce leakage of body exudates from diaper 210, the diaper side margins and end margins may be elasticized with suitable elastic members, such as single or multiple strands of elastic. The elastic strands may be composed of natural or synthetic rubber, and may optionally be heat-shrinkable or heat-elasticizable. Elastic members 260 and 262 are constructed to operably gather and shirr side margins 226 and 228 to provide elasticized leg bands which can closely fit around the legs of the wearer to reduce leakage and provide improved comfort and appearance. Similarly, waist elastic members 264 and 266 can be employed to elasticize diaper end margins 222 and 224 to provide elasticized waistbands. The waist elastics are configured to operably gather and shirr the waistband sections to provide a resilient, comfortably close fit around the waist of the wearer.

Backsheet 220 is composed of a substantially liquid impermeable material, which is also gas impermeable but may optionally be gas/vapor permeable. In the illustrated embodiment, the backsheet is substantially impermeable to water and water vapor. An example of a suitable backsheet material is a polymer film composed of polyethylene, polypropylene, or the like. Typically, the polymer film has a thickness within the range of about 0.0007–0.002 inch (0.0018–0.0051 cm). Backsheet 220 may alternatively be composed of a nonwoven fibrous web constructed to provide the desired levels of fluid impermeability. For example, a nonwoven web composed of spunbonded or meltblown polymer fibers may be selectively treated with a water repellent coating, or laminated with a fluid impermeable, polymer film.

In alternative embodiments of the invention, backsheet 220 may comprise a nonwoven web composed of a plurality of randomly deposited hydrophobic thermoplastic meltblown fibers which are sufficiently bonded or otherwise connected to one another to provide a substantially vapor impermeable and substantially liquid impermeable web. The backsheet may also comprise a vapor permeable nonwoven layer which has been partially coated or otherwise configured to provide liquid impermeability only in selected areas, leaving the remaining areas vapor permeable.

Topsheet 230 is typically composed of a liquid permeable, substantially hydrophobic fibrous material, such as a spunbonded web composed of synthetic polymer filaments. Alternatively, topsheet 30 may comprise a meltblown web or a bonded-carded-web composed of synthetic polymer filaments. Suitable synthetic polymers include, for example, polyethylene, polypropylene and polyesters. In a particular aspect of the invention, the polymer filaments have a denier within the range of about 1.5-7 d and preferably have a denier within the range of about 1.5-3 d to provide improved performance. The filaments are arranged to form a layer having a basis weight within the range of about 8-34 gm/m$^2$ (gsm), and preferably are arranged to have a basis weight of about 27 gsm. In addition, the topsheet layer has a bulk thickness within the range of about 0.008-0.017 inches (about 0.0203-0.0432 cm), and preferably has a bulk thickness within the range of about 0.010-0.12 inches (about 0.0254-0.305 cm) for improved effectiveness. The bulk thickness is measured under a restraining pressure of 0.014 psi (0.096 kPa).

Topsheet 230 may optionally be treated with surfactants to adjust its degree of hydrophobicity and wettability. It can also be selectively embossed or apertured with discrete slits or holes 232 extending therethrough.

Absorbent body 240 comprises an integral mass of hydrophilic material which is typically configured to form a fibrous absorbent pad layer. The hydrophilic fibers can, for example, be composed of a fibrous cellulosic material commonly referred to as woodpulp fluff, and can be airlaid to form an integral fibrous pad. Other fibers, such as cotton and synthetic polymer fibers, may also be employed to form the pad. Conventional absorbent pads can have a density ranging from about 0.05-0.20 grams/cc, and are sufficiently flexible to readily conform to the body shape of the wearer. In particular arrangements, the fibrous material comprising the pad may be nonuniformly distributed over the pad length and width. For example, see U.S. Pat. No. 4,585,448, "Disposable Garment Having High-Absorbency Area", issued Apr. 29, 1986 to K. Enloe.

Absorbent body 240 may alternatively include an integral layer of a fibrous coform material composed of a mixture of cellulosic fibers and synthetic polymer fibers. For example, the coform material may be composed of an airlaid blend of cellulosic fibers and meltblown polyolefin fibers, such as polyethylene and/or polypropylene fibers. In one aspect of the invention, the fibrous material comprising absorbent body 240 is composed of filaments having a coarseness of about 10-20 mg/100 meters, and preferably having a coarseness within the range of about 10-18 mg/100 meters. The filaments are arranged to form a layer having a basis weight within the range of about 400-1200 gsm, and preferably having a basis weight of about 800 gsm. In addition, the absorbent body material typically has a bulk thickness within the range of about 0.17-0.21 inches (about 0.432-0.533 cm), as measured under a restraining pressure of 0.068 psi (0.47 kPa).

To increase the absorbent capacity of absorbent body 240, it has been desireable to add quantities of relatively high-absorbency material to the fibers comprising the absorbent body. Such high-absorbency materials are capable of holding, on a weight basis, at least about 15 parts of water per part of high-absorbency material. Preferably, the high absorbency material is capable of holding at least about 50 parts of water per part of high-absorbency material.

Absorbent body 240 should include an effective amount of the high-absorbency material to operably enhance the absorptive capacity of the absorbent body. For example, absorbent body 240 can contain 5-95 weight percent high-absorbency material, and preferably includes about 10-30 weight percent of the high-absorbency material to provide more efficient performance.

The high-absorbency material material has typically been distributed or otherwise incorporated into absorbent body 240 by employing various techniques. For example, the high-absorbency material can be incorporated into a separate carrier sheet which is layered with a body of airlaid cellulosic fibers. Alternatively, the high-absorbency material may be substantially uniformly distributed and mixed within the mass of fibers comprising the absorbent body. The material can also be non-uniformly distributed among the fibers to form, for example, a generally continuous gradient with either an increasing or decreasing concentration of high-absorbency material, as determined by observing the concentration moving from the body-side of absorbent body 240 toward the outer-side of the absorbent body. The high-absorbency material may also be substantially unmixed with the fibrous material of absorbent body 240, and may comprise one or more discrete layers or strips selectively segregated from the fibrous material.

Optionally, a substantially hydrophilic tissue wrap 242 may be employed to help maintain the integrity of the airlaid fibrous structure of absorbent body 240. The tissue wrap sheet is typically placed about the absorbent body over at least the two major facing surfaces thereof, and composed of an absorbent cellulosic material, such as creped wadding or a high wet-strength tissue.

In the article aspect of the invention, absorbent body 240 has the structural configuration of a concurrently airlaid mixture of hydrophilic fibers and superabsorbent particles. The fibers and particles are concurrently formed into a substantially integral web layer while the fibers and particles are non-homogeneously intermingled with each other. In such structure, the superabsorbent particles are not substantially isolated in a discrete superabsorbent layer. The resultant absorbent body can include a distinctive, selectively varied distribution of superabsorbent particles along the longitudinal length dimension 142 of the absorbent body. For example, the average weight percentage of superabsorbent particles can be nonuniformly distributed along said length dimension.

It is recognized that there may also be some variations in the concentration of superabsorbent particles along the cross-direction 144 of absorbent body 240. Accordingly, for the purposes of the present invention, the distribution of superabsorbent particles should be considered in the context of a representative, functional region located substantially along and about the longitudinal center line 146 of the absorbent body. It will be appreciated that the particular dimensions and shape of the functional region will depend upon the intended use, and the size and configuration of the overall absorbent body. The superabsorbent concentration at a particular, chosen location along the length of the absorbent body will be an average concentration taken over the cross-directional width of the absorbent body at that location.

The intermixed configuration of the superabsorbent particles and fibrous material is desireable because it can provide an advantageous combination of capillarity, interfiber void volume and total absorbent capacity. The fibrous material contributes to the capillarity and interfiber void volume, while the superabsorbent particles contribute to the total absorbent capacity. The fiber capillarity helps provide a rapid movement and wicking of liquid through the absorbent body and the interfiber void volume helps provide a rapid rate of liquid uptake into the absorbent body. In addition, the intermingled configuration of the particles and fibrous material helps improve the mechanical integrity of the total structure.

Figure 11:
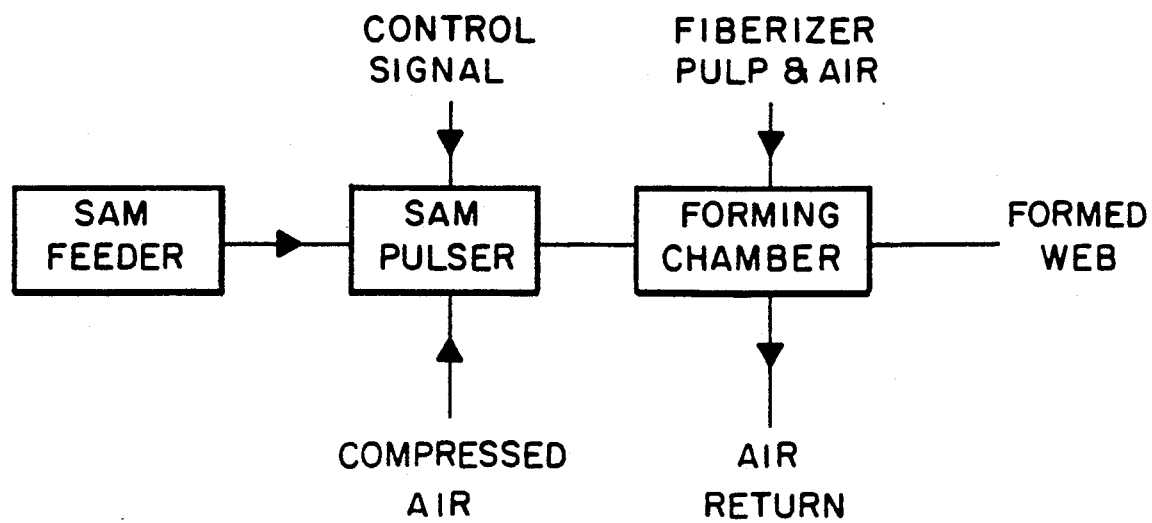
FIGS. 11 and 11A show a schematic block diagram of a pulser-type system, and a graphic representation of the distribution of particulate material produced along a longitudinal dimension of a fibrous web by such a system, respectively.
Figure 11A:
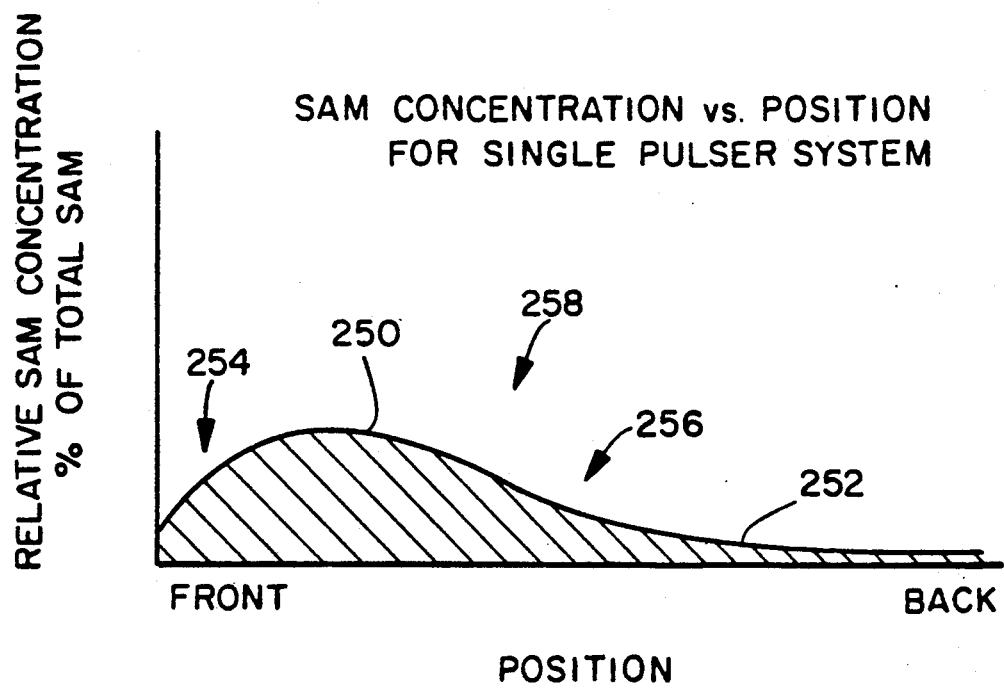

As representatively shown in the graph of FIG. 11A, absorbent body 240 can advantageously include a nonuniform distribution of superabsorbent particles having the arrangement of a substantially continuous gradient of concentrations along longitudinal length dimension 142. In the illustrated embodiment, the superabsorbent concentration gradient continuously increases and decreases in a non-step-wise arrangement. The particles are selectively arranged in an airlaid, dispersed structure to provide a distinctive, non-homogeneous mixture within the substantially integral fibrous layer comprising the absorbent body. The particles are in a non-layered configuration, and are not substantially isolated within a discrete layered zone wherein the particles are substantially unmixed with fibrous material.

While the absorbent body may or may not include absorbent particles along its total length, the present invention can advantageously provide a configuration of the absorbent body wherein a greater amount of particles are located at selected positions along the length of the absorbent body and wherein the particles are substantially non-homogeneously mixed within the associated, intermingled quantity of fibrous material located at those selected positions. Accordingly, a greater (or smaller) proportion of superabsorbent particles may be located at the selected positions along the length of the absorbent body without also locating a corresponding, greater (or smaller) proportion of the fibrous material at those selected positions. In particular aspects of the invention, a greater proportion of superabsorbent particles may be located at the selected, length-wise positions of the absorbent body without also locating a corresponding, greater basis weight (weight per unit area) of the fibrous material at those selected positions. Conversely, a lesser proportion of superabsorbent particles may be located at selected positions along the length of the absorbent body without also locating a corresponding, smaller basis weight (weight per unit area) of fibrous material at those selected positions.

Thus, the concentration of superabsorbent particles at a particular location may be configured to be substantially independent of the amount (e.g. basis weight) of fibrous material at that location. When one observes different contiguous sections taken form along the length of the absorbent body, the amount of particulate material does not rise and fall in a substantially direct correspondence with a rise and fall of the amount of fibrous material in those sections. A particular embodiment of the invention, for example, can comprise an arrangement wherein the local amount of particulate material does not rise and fall in correspondence with a rise and fall of the local basis weight (weight per unit area) of the fibrous material in that section. Other embodiments can similarly be configured wherein the weight percentage of the total amount of superabsorbent or the weight of superabsorbent per unit area is nonuniformly distributed along the length of the article in a substantially continuous distribution profile, but does not change (rise and/or fall) in a substantially direct correspondence with the length-wise change in the local basis weight or local weight-percentage level of the associated fibrous material.

In a preferred embodiment, a greater proportion of superabsorbent particles may be concentrated toward at least one longitudinal end of the absorbent body without a corresponding greater proportion (e.g. basis weight) of the fibrous material also being concentrated at that end of the absorbent body. In a more specific embodiment, the particles can be concentrated toward the front waistband end 148 of the absorbent body. As a result, the superabsorbent can be more efficiently located in those regions which typically are more heavily wetted by the wearer, and lesser amounts of superabsorbent material can be located in those regions which typically receive lesser amounts of liquid. The effective level of total absorbency of the absorbent body can thereby be improved or maintained while using the same or lesser amounts of the relatively expensive superabsorbent material.

In particular aspects of the invention, at least about 50 wt % and not more than about 95 wt % of the total amount of superabsorbent particles are located in the front 50% of the overall length of absorbent body 240. Preferably, about 55–85 wt % and more preferably, about 60–85 wt % of the total amount of superabsorbent particles are located in the front 50% of the overall absorbent body length. Such weight percentages of superabsorbent, however, are not present in combination with corresponding, similar weight percentages of the total amount of fibrous material. For example, the front 50% of the length of absorbent body 240 may include 60–80 wt % of the total amount of superabsorbent but only include 55 wt % of the total amount of fibrous, fluff material. As another example, the front 50% of the absorbent body may include 60–80 wt % of the total amount of superabsorbent, but only include 40–50 wt % of the total amount of fibrous material.

In further embodiments of the invention, relatively higher weight percentages of the superabsorbent material can be selectively located at predetermined locations along the length of absorbent body 240. For example, 50–60 wt % of the total amount of fibrous material may be located in a front 45% of the absorbent body while 50–80 wt % of the total amount of superabsorbent is located in a middle 30% of the absorbent body. Thus, the region having the maximum weight percentage of intermixed fibrous material can be offset lengthwise from the region having the maximum weight percentage of intermixed superabsorbent material.

The article aspect of the invention can advantageously be constructed to provide a distinctive absorbent body comprising a plurality of two or more different types of superabsorbent material, with each type characterized by it own predetermined set of functional parameters. For example, different types of superabsorbent materials can have different values for shear modulus, grams of liquid absorbed per gram of superabsorbent material, rate of absorption of liquid, gel strength, ability to swell under compressive load, cost etc. As a result, particular types of different superabsorbents can be selectively chosen to provide a desired combination of functional characteristics which may not be available from a single type of superabsorbent material. In addition, the different types of superabsorbent material may be selectively positioned along the length, width or thickness of the absorbent body to more effectively take advantage of the particular characteristics afforded by each type of superabsorbent.

Referring now to FIG. 11A, a representative pulsing system of the invention (FIG. 11) can advantageously produce along the length of absorbent body 240 a particle distribution having the general shape of an inverted spoon. The particle distribution provides a substantially continuous, non-step-wise gradient of particulate concentrations. The gradient is generally aligned and extends along the length of the absorbent body. The substantially continuous distribution profile has a bowl section 250 which represents major concentrations of relatively larger amounts of particles and a handle section 252 which represents the lesser concentrations or amounts of particles. Beginning at the front waistband edge of absorbent body 240, the weight percent of superabsorbent particles, determined with respect to a selected total amount of superabsorbent within absorbent body 240, is less than about 30 weight percent. Preferably, the proportion of superabsorbent particles is less than about 20 wt %, and more preferably is less than about 10 wt %. The weight percentage of particles gradually rises in the "increasing" section 254 of the distribution profile until it reaches a maximum at a location within the range of approximately 5-30% of the total length of the absorbent body. The maximum, peak proportional amount of superabsorbent particles is typically not more than about 40 wt %. After reaching the peak weight percent, the concentration of superabsorbent particles gradually falls in the "decreasing" section 256 of the profile until it reaches a value of less than about 30 weight percent at a region positioned at about 40-90% of the absorbent body length away from the front waistband edge. Preferably, the proportion of superabsorbent particles is less than about 20 wt % and more preferably is less than about 8 wt % within this region of the absorbent body.

Figure 12:
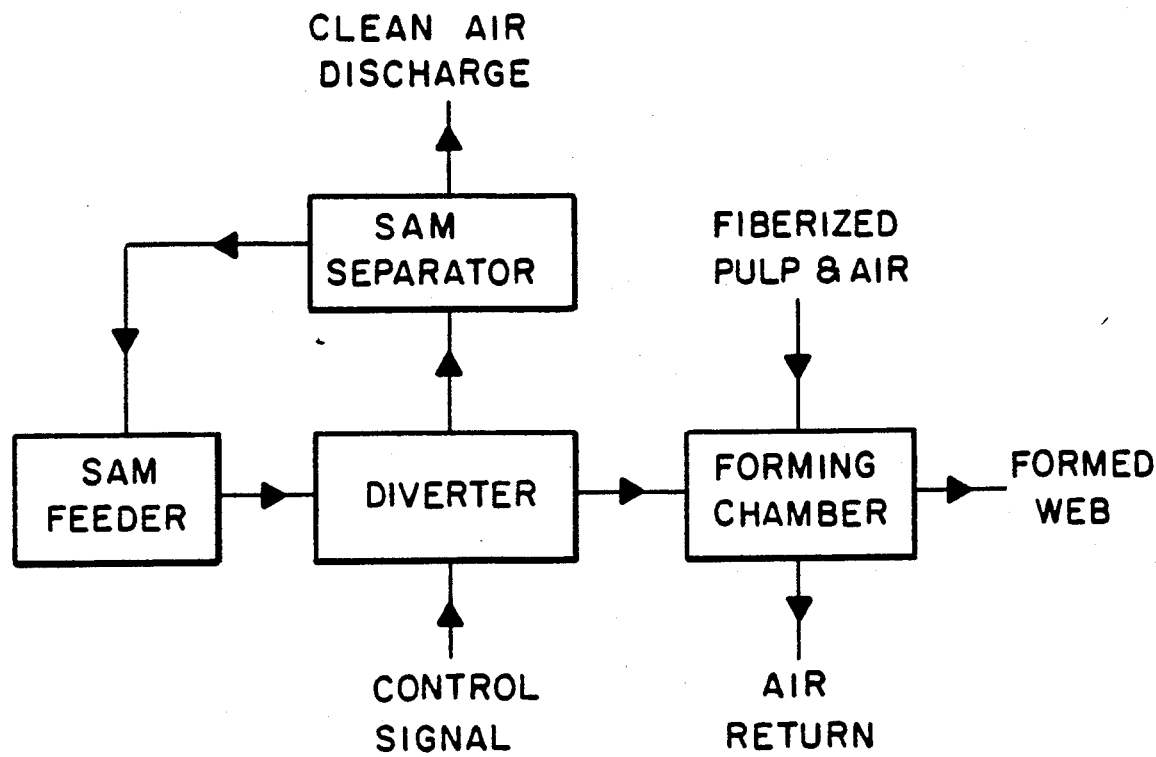
FIGS. 12 and 12A show a schematic block diagram of a diverter-type system, and a graphic representation of the distribution of particulate material produced along the longitudinal dimension of the fibrous web by such a system, respectively.
Figure 12A:
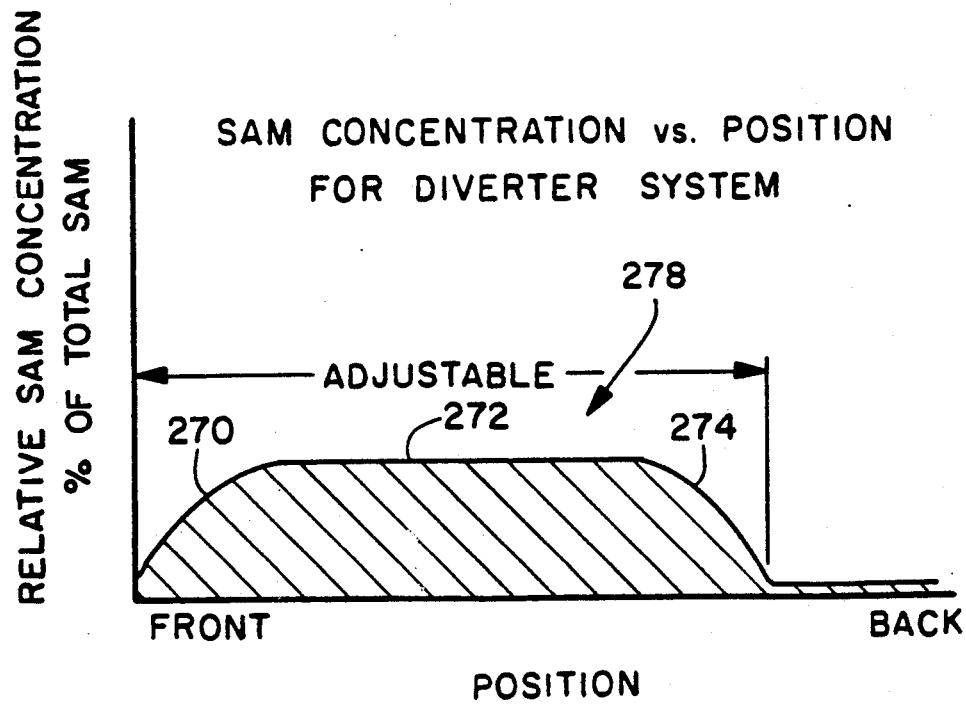

FIG. 12A representatively shows a particle distribution produced by the embodiment of the invention (FIG. 12) which includes a diverter-type system for producing intermittent particle flows. The diverter-type system can advantageously produce along the length of absorbent body 240 a substantially continuous particle distribution having the general shape of a plateau. The particle distribution has an "increasing" section 270 in which the superabsorbent concentrations are rapidly rising, a plateau section 272 in which the maximum superabsorbent concentrations remain substantially constant, and a "decreasing" section 274 in which the superabsorbent concentrations are rapidly falling. Beginning at the front waistband edge of absorbent body 240, the weight percent of superabsorbent particles, determined with respect to a unit weight of absorbent body 240, is less than about 25 weight percent. Preferably, the proportion of superabsorbent particles is less than about 20 wt %, and more preferably is less than about 10 wt %. The weight percentage of particles gradually increases until it reaches a plateau maximum at a location within the range of approximately 5-30% of the total length of the absorbent body. The proportional amounts of superabsorbent particles along the plateau section of the distribution are typically not more than about 40 wt %. After reaching the end of the plateau section, the concentration of superabsorbent particles decreases in the "falling" region of the distribution until it becomes less than about 30 weight percent at a region positioned at about 40-90% of the absorbent body length away from the front waistband edge thereof. Preferably, the concentration of superabsorbent particles decreases to a level which is less than about 20 wt %, and more preferably decreases to a level which is less than about 8 wt %.

The distribution of superabsorbent particles within the absorbent body may also be distinctively configured with two or more stages. FIG. 13A, for example, representatively shows a superabsorbent particle distribution produced by an embodiment of the invention which includes a combination of two pulsing systems (FIG. 13). The two pulser-type systems may deliver the same type or different types of superabsorbent material. In the illustrated embodiment, the first quantity of superabsorbent particles provided by the first pulser mechanism (distribution profile 255) is positioned relatively closer to the front waistband end of the absorbent article, and the second quantity of superabsorbent particles delivered by the second pulser mechanism (distribution profile 257) is positioned relatively closer to the back waistband end of the article. Accordingly, the two types of superabsorbent have different positional arrangements along the length dimension of the article. The illustrated arrangement includes a selected amount of overlap between the first and second quantities of superabsorbent within the single, integral layer of absorbent fibers. As a result, there is a distinctive step-wise, "stacked" change in the overall, composite superabsorbent distribution 259 along the length dimension of the article, and the distribution is in part distinguished by at least two discrete, interconnected stages in the "increasing" segment 253 of the composite superabsorbent distribution.

FIG. 14A representatively shows a particle distribution produced by an embodiment of the invention which includes, in combination, a pulser-type system and a diverter-type system (FIG. 14). Such a combination-type system can advantageously produce an absorbent body having a combination of the spoon-shaped, superabsorbent distribution profile 258 and plateau-shaped distribution profile 278. The combination system can also be configured to deliver different types of superabsorbent into the formation of the absorbent body. The shown embodiment of this arrangement includes a superabsorbent distribution wherein a first quantity of particulate material provided by the pulser-type system is arranged in the spoon-shaped section 258 of the distribution. The spoon-shaped section is offset towards the front waistband edge of the absorbent body, and overlaps with the plateau-shaped section 278 of the superabsorbent distribution produced by a second quantity of particulate material provided by the diverter-type system. As a result, there is a distinctive step-wise, "stacked" change in the overall, composite superabsorbent distribution along the length dimension of the article, and the composite distribution 280 is in part distinguished by at least two discrete stages in the "decreasing" segments 282 of the composite superabsorbent distribution. In alternative arrangements of this aspect of the invention, the relative positions and degree of overlap of the first and second quantities of particulate material may be changed. Accordingly, there may be two or more discrete stages in either or both of the "increasing" and "decreasing" segments of the composite superabsorbent distribution.

Figure 15:
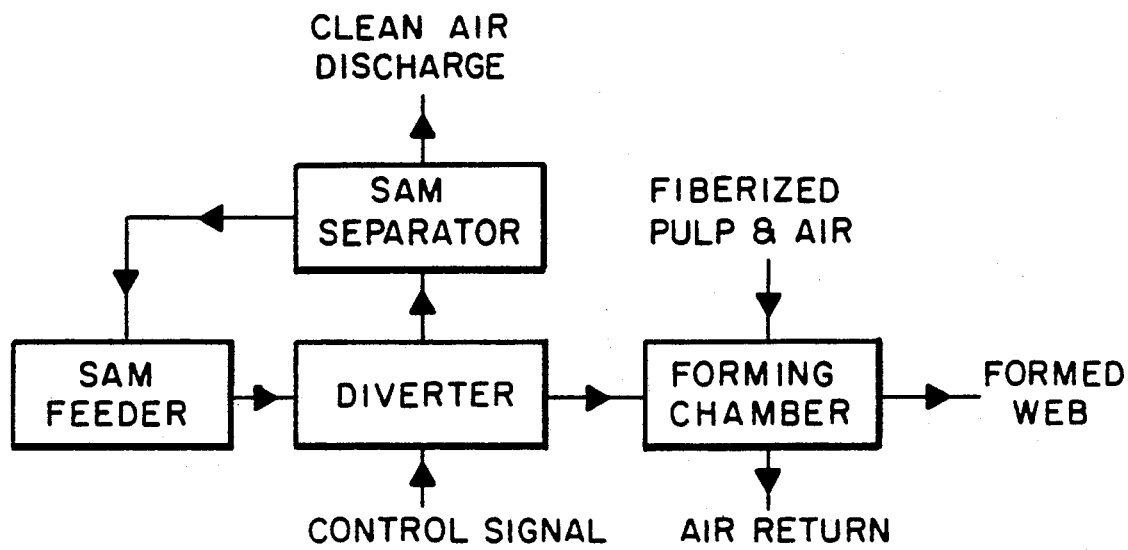
FIGS. 15, 15A and 15B respectively show a schematic block diagram of a diverter-type system capable of providing a plurality of discrete open positions, examples of three discrete diverter positions, and a graphic representation of the distribution of particulate material produced along the longitudinal dimension of the fibrous web by such a system.
Figure 15A:
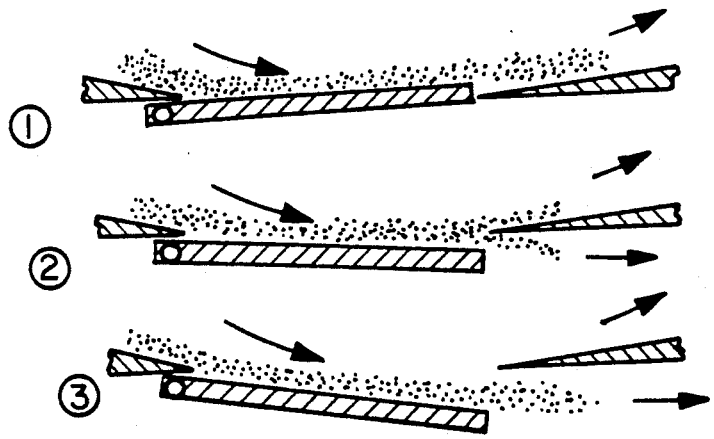
Figure 15B:
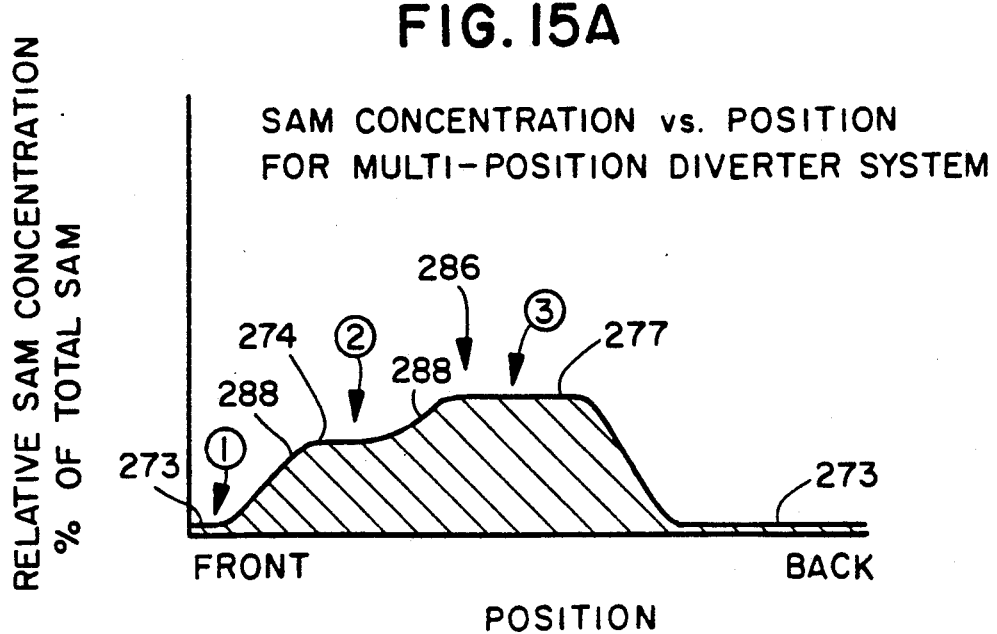

FIG. 15B representatively shows a particle distribution produced by an embodiment of the invention which includes a multiple-position, diverter-type system (FIG. 15 and 15A). Such a system can advantageously produce an absorbent body having a combination of two or more interconnected plateau-shaped superabsorbent distributions, which are sequentially located contiguous with each other. The shown embodiment of the absorbent body is distinguished by a superabsorbent distribution (FIG. 15B) wherein a first quantity of particulate material is arranged in a first, base section 273 of the distribution, a second quantity of particulate material is arranged in a second, serially located plateau section 274 of the distribution and a third quantity of particulate material is arranged in a third, serially located plateau section 277 of the distribution. The first quantity of particulate material is provided when the diverter-type system is at a first, closed position while a base distribution is being delivered into the absorbent body by conventional means (not shown). The second quantity of particulate material is provided when the diverter-type system is actuated to a second partially open position (FIG. 15A (2)) to produce a plateau in the distribution having a first plateau value in section 274. The second quantity of particulate material is provided when the diverter-type system is actuated to a third, fully open position (FIG. 15A at (3)) to produce a plateau in the distribution having a second, maximum plateau value in section 277. Since the three contiguous and interconnected sections of the composite distribution have different characteristic values for the concentrations of particulate material, there is a distinctive step-wise change in the overall, composite superabsorbent distribution along the length dimension of the article, and the composite distribution 286 is in part distinguished by at least two discrete stages in the "increasing" segments 288 of the composite particulate distribution. In alternative arrangements of this aspect of the invention, the relative maximum values and the relative sequential relationships of the individual plateau sections material may be changed. Accordingly, there may be two or more discrete stages in either or both of the "increasing" and "decreasing" segments of the composite particulate distribution.

Figure 16:
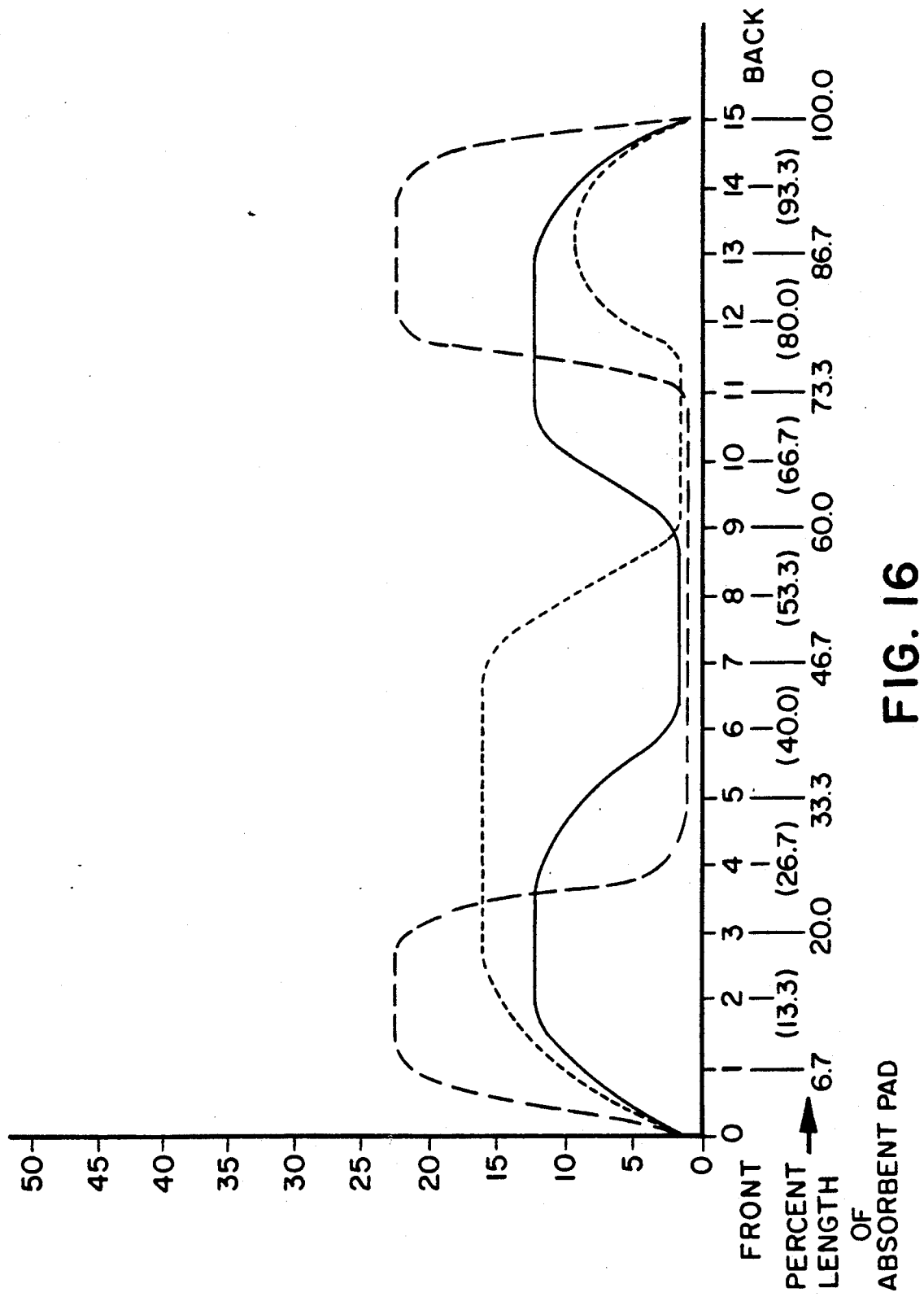
FIG. 16 shows a graphic representation of several bilobal distributions of particulate material produced along the longitudinal dimension of the fibrous web.

FIG. 16 representatively shows an alternative particle distribution which can be produced with a combination system or with a multiple position, diverter-type system of the present invention. In the illustrated embodiment, the superabsorbent distribution has a distinctive "bilobal" shape with the relatively greater amounts of superabsorbent at the front and rear waistband ends of the absorbent layer and with relatively smaller amounts of superabsorbent at the intermediate section of the absorbent layer. Accordingly, the graphic representation of the superabsorbent distribution increases in two discrete stages, but the step-wise stages are "unstacked" and are serially and separately positioned in discrete, spaced relation along the length of the absorbent layer. In the shown embodiment, the proportional amounts of superabsorbent at the various measured locations along the length of the absorbent layer are determined in terms of weight percentage of the total amount of superabsorbent contained within the overall region of the absorbent body taken for analysis and measurement.

The following examples are provided to afford a more detailed understanding of the invention. The particular materials, proportions and other parameters are exemplary and are not intended to specifically limit the scope of the invention.

EXAMPLE 1

Disposable diapers were constructed in accordance with the present invention. Each of the diapers included an absorbent body comprising a non-homogeneous mixture of cellulosic woodpulp fluff and superabsorbent particles composed of a sodium polyacrylate superabsorbent hydrogel material (SAM). In the manufacture of the diapers, the fibrous woodpulp fluff and superabsorbent particles were concurrently airlaid to form an integral fibrous web, and a diverter-type system was employed to deliver the superabsorbent particles into the airlaying process. The airlaid web was wrapped with a high wet-strength cellulosic tissue wrap, and the wrapped web was separated and shaped into individual absorbent bodies, commonly referred to as absorbent pads. The pad were used to manufacture disposable diapers. The basis weight of the fluff within the pads was nonuniform, ranging between approximately 380-830 gm/m$^2$, with the higher basis weight regions positioned towards the front waistband edge of the pads. The pads had an overall, I-shape with a longitudinal length of about 15 inches (about 38.1 cm).

Figure 17A:
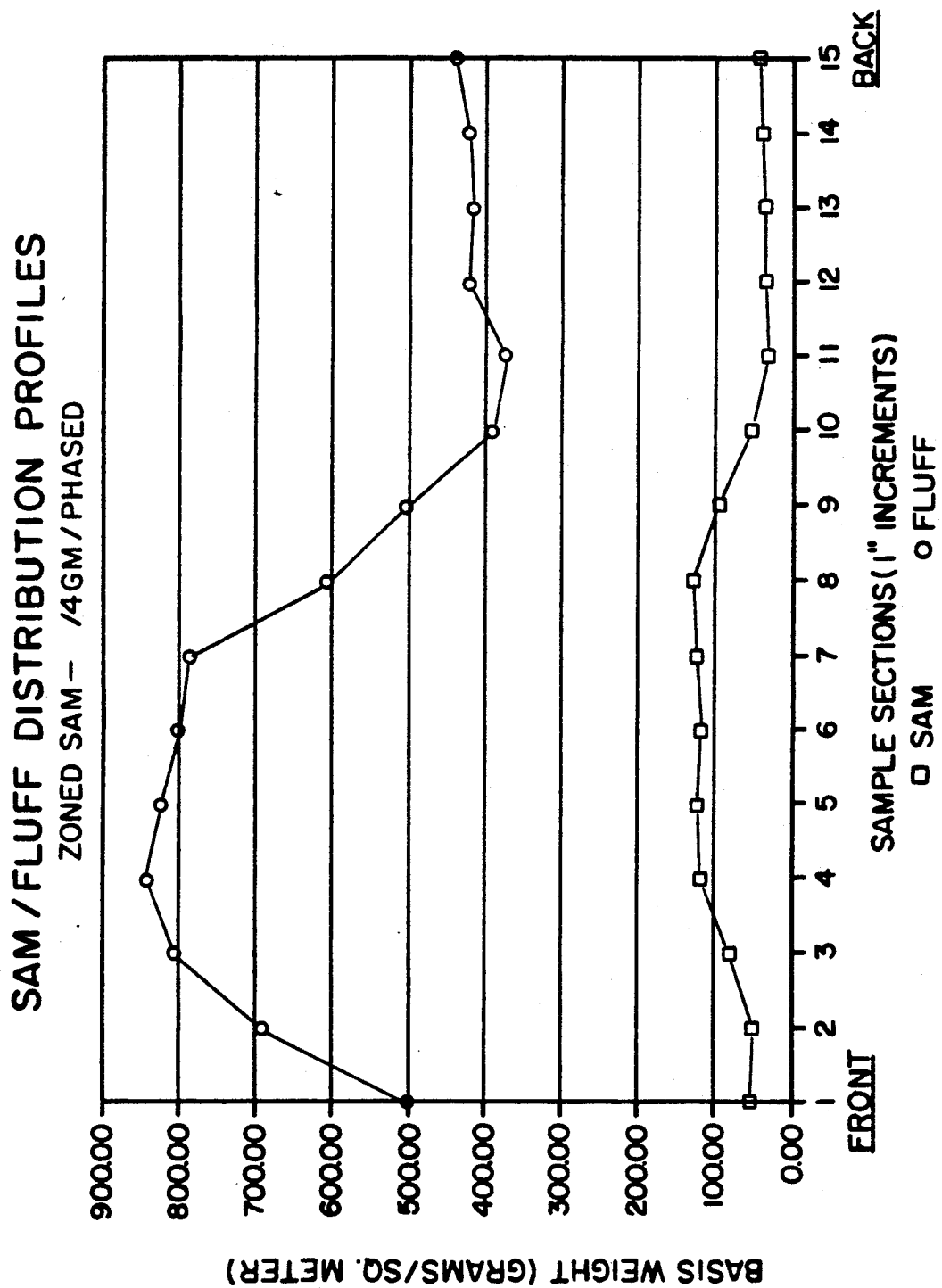

For the purpose of determining the superabsorbent distribution profile, test sections were cut for ten substantially identical diaper pads. Each test section was taken from a pad region centered about the diaper longitudinal centerline. Each pad test section, which measured 15 inches long and 5.5 inches wide, was then cut into 15 individual, numbered test samples (#1-#15), each of which measured 1 inch by 5.5 inches. Accordingly, there was a group of ten #1-samples, a group of ten #2-samples, a group of ten #3-samples and so on, thereby providing 15 sample groups. The average weight of superabsorbent per numbered sample for each of the 15 groups was then determined. After determining the average total weight of superabsorbent for an individual, entire test section, the average weight percentage per numbered sample (averaged over the 10 samples in the corresponding sample group) was calculated. The resultant data were employed to plot the graph representatively shown in FIGS. 17 and 17A.

Various conventional techniques may be employed to determine the quantitative amount of superabsorbent material within a test a sample. Suitable analytical techniques include, for example, a sulfated ash measurement method, such as described in *Vogel's Textbook of Quantitative Inorganic Analysis*, Fourth edition, revised by J. Bassett, R. C. Denney, G. H. Jeffery, J. Mendham, Longman Inc., 1978, pp. 479-481. Another suitable technique would be an ion exchange method (e.g. sodium ion exchange), such as described in *Treatise on Analytical Chemistry*, Volume 1, edited by I. M. Kolthoff and Phillip J. Elving, Interscience Publishers, Inc., 1961, pp. 345-350. Further suitable techniques include atomic absorption methods, such as described in *Vogel's Textbook of Quantitative Inorganic Analysis*, Fourth edition, revised by J. Bassett, R. C. Denney, G. H. Jeffery, J. Mendham, Longman Inc., 1978, pp. 810-845. The *Encyclopedia of Industrial Chemical Analysis*, Volume 18, edited by Foster Dee Snell and Leslie S. Ettre, Interscience Publishers, Inc., division of John Wiley & Sons, 1973, at pp. 207-259 further describes well known, conventional techniques for quantitatively measuring the amount of sodium within a sample.

In the analyses conducted for the purposes of the present Examples, the quantitative determinations were made by an ion exchange method. Since the chemical compositions of the superabsorbent polymers employed in the Examples included particular, known proportions of sodium, a sodium selective ion detection method was employed. This technique measured the quantitative amounts of sodium and then employed the resultant measurements to derive the associated, corresponding amounts of superabsorbent polymer.

In particular, the test samples of absorbent pad undergoing quantitative analysis were intimately and completely mixed in a mixing container with a sodium containing a suitable exchange ion, such as ions of potassium, calcium, lithium or ammonium. The solution was sufficiently concentrated to force the sodium out of the superabsorbent polymer and into the solution. For the analyses of the present Examples, the solution contained about a 0.3 molar concentration of the exchange ion, and approximately 30 ml of solution was mixed per gram of pad material.

After a thorough mixing of the sample pad material in the solution, a sodium specific electrode was employed to detect the amount of sodium ions in the resultant, mixed solution. The output from the electrode was processed by an ion analyzing electrode meter. A suitable electrode is a ROSS TM Sodium Electrode, Model 84-11, and a suitable ion analyzer is an ORION pH/ISE meter, Model EA-940. Each of these devices is available from Orion Research, Inc., a business having offices at Schrafft Center in Boston, Mass. The electrode was appropriately calibrated employing "known" standard solutions, in accordance with its associated instructional manual. The standard solutions were composed of ion exchange solutions which had been mixed with specific, known amounts of the particular superabsorbent material contained in the pads, and at least three different standard solutions were used to calibrate the electrode. The electrode meter was appropriately programmed/calibrated to provide a read-out in terms of grams of superabsorbent. The programming procedure was described in the instruction manual provided with the device.

It will be readily appreciated that articles made in accordance with the present invention may contain superabsorbent materials having chemical compositions different than that of the superabsorbent employed in the Examples. Such different superabsorbents may not contain sodium but would contain some other characteristic chemical component. Accordingly, the selected analytical technique for quantitatively measuring the amount of superabsorbent may need to be adjusted to target the particular, characteristic component present in those compositions. The manner of such adjustment would be readily apparent to persons of ordinary skill in the analytical arts.

Figure 18:
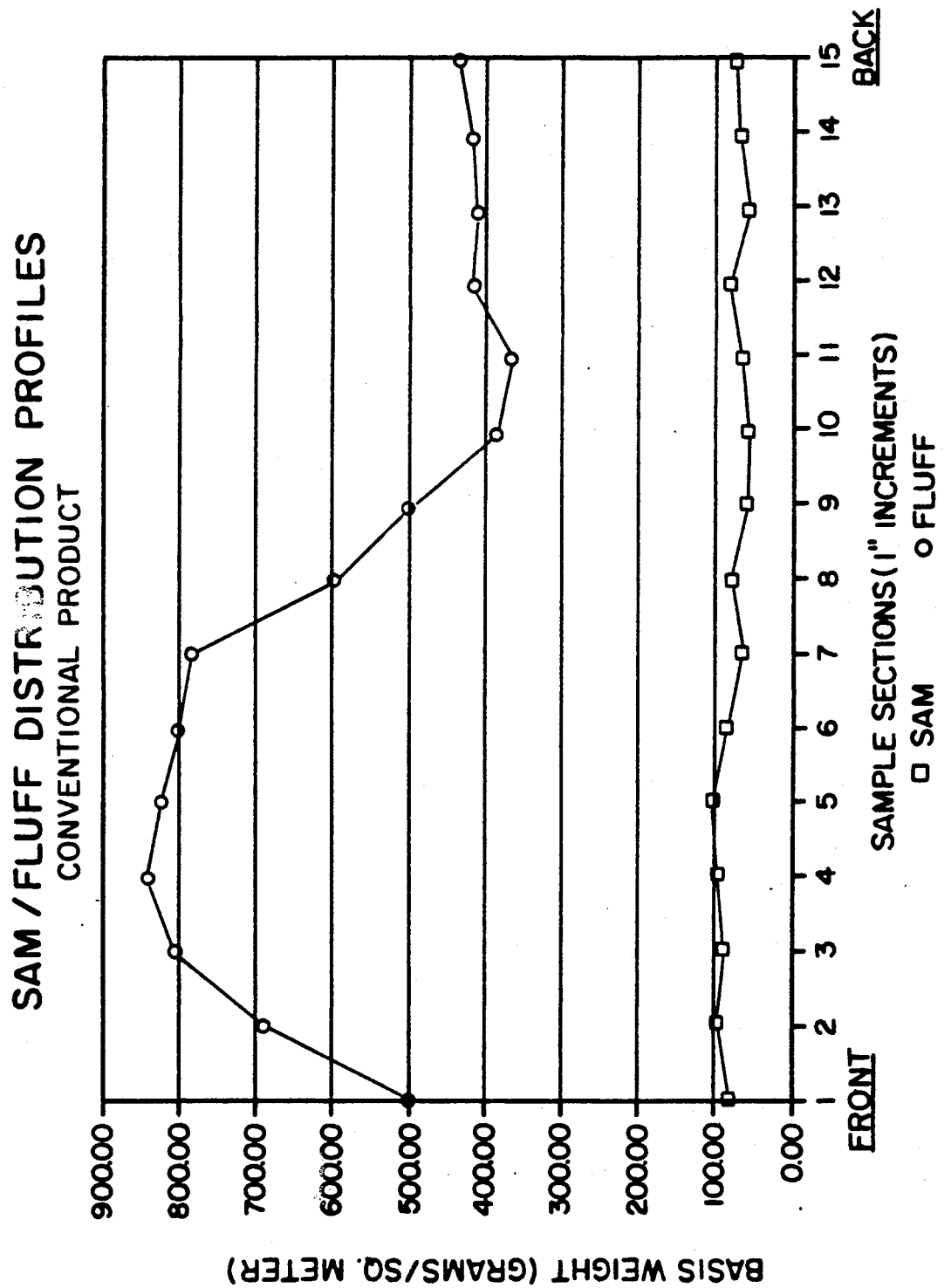
FIG. 18 shows a graphic representation of sequential regions along the length of a conventional diaper wherein the superabsorbent particles are substantially uniformly distributed along the diaper length.

For comparison purposes, pads from a conventional diaper product were analyzed in accordance with the technique employed in this Example 1. Referring to FIG. 18 which graphically represents the relative amounts of superabsorbent and fibrous fluff along the length of the conventional diaper, it can be seen that on the average the particles of superabsorbent were substantially uniformly distributed along the length of the conventional diaper pad.

EXAMPLE 2

Figure 19:
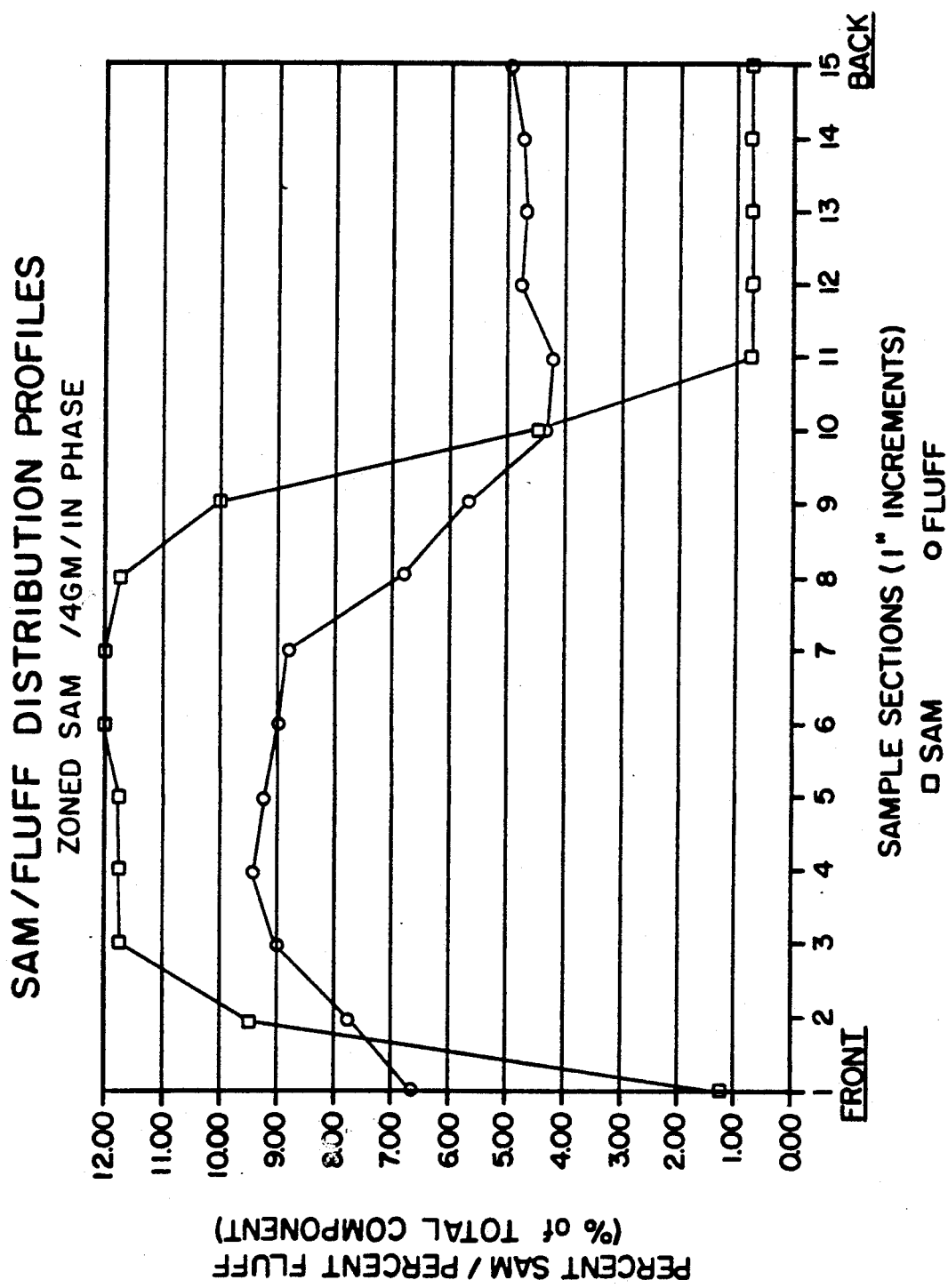
FIGS. 19 and 19A show graphic representations of regions along the length of an article of the invention wherein article regions with higher amounts of superabsorbent are in-phase with article regions with higher amounts of fibrous material.
Figure 19A:
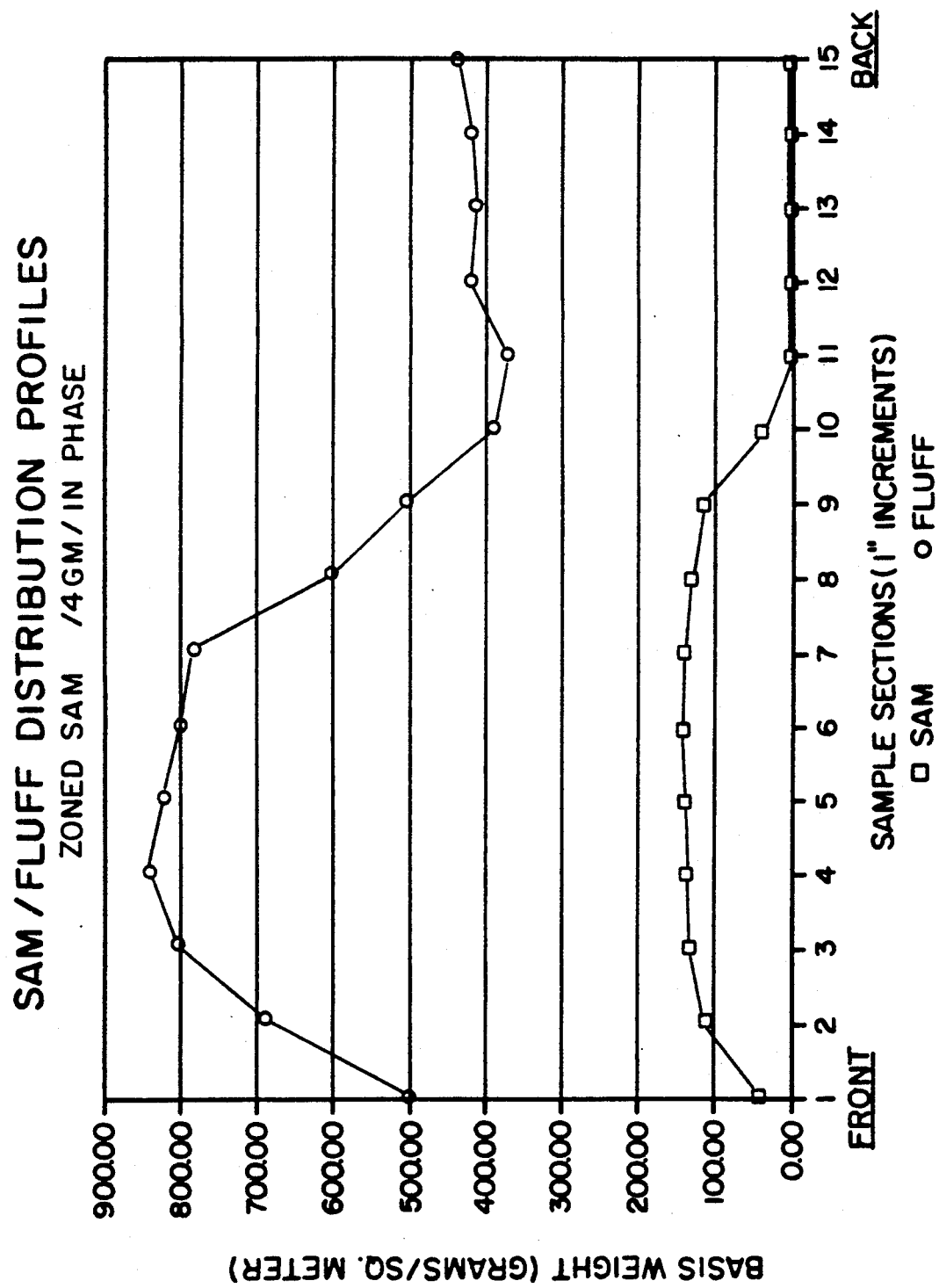

Disposable diapers are constructed in accordance with Example 1. Each of the diapers includes an absorbent body comprising a nonhomogeneous mixture of cellulosic woodpulp fluff and superabsorbent particles composed of sodium polyacrylate superabsorbent hydrogel material (SAM). Test sections of the diapers are analyzed in accordance with Example 1 and exhibit the relative amounts of fluff and superabsorbent material graphically represented in FIGS. 19 and 19A. In these diapers, the regions of increased levels of superabsorbent are substantially "in phase" with the regions of increased levels of fluff.

Figure 19B:
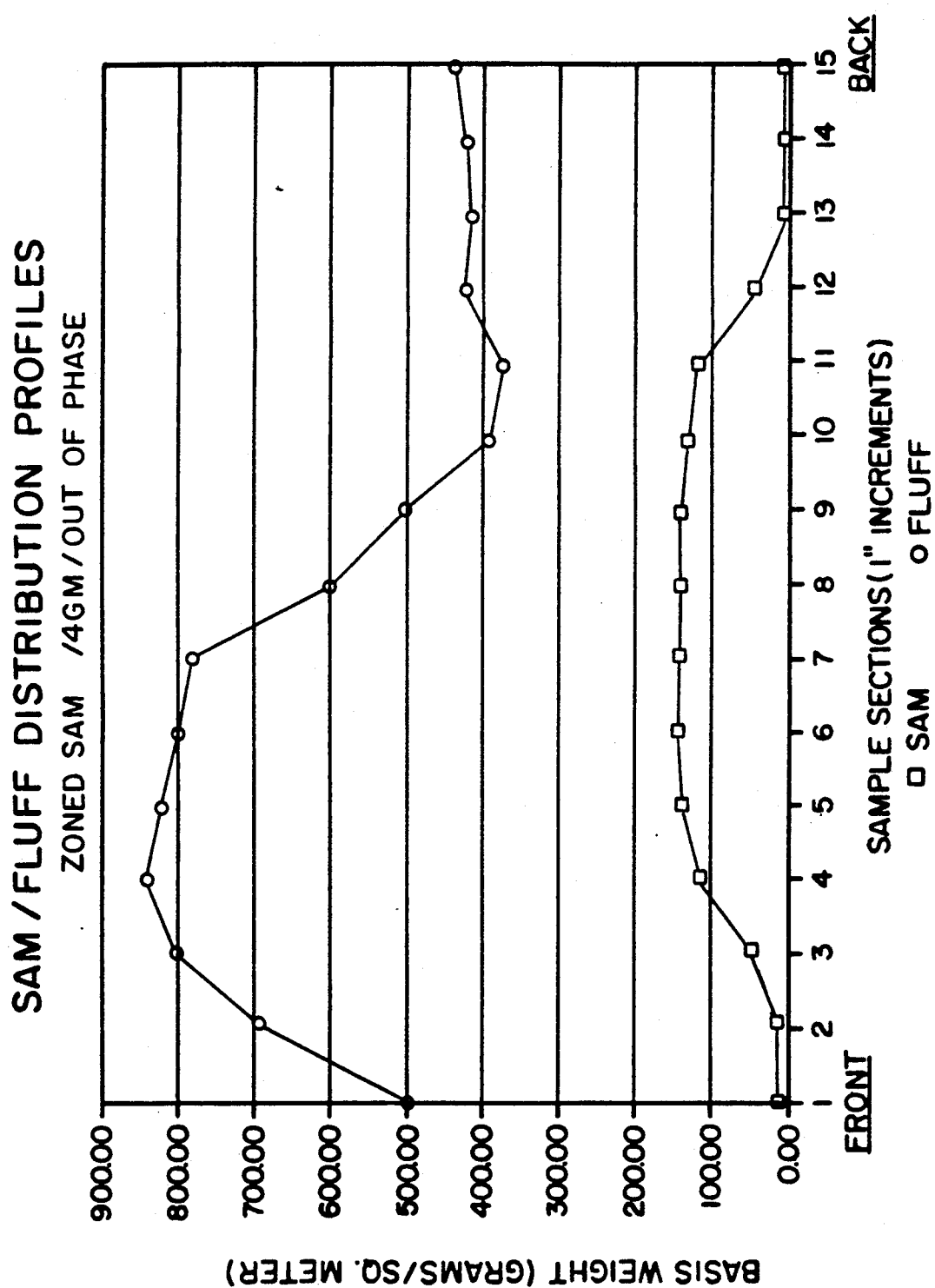
FIG. 19B shows a graphic representation of regions along the length of an article of the invention wherein article regions with higher amounts of superabsorbent are out-of-phase with article regions with higher amounts of fibrous material.

Additional diapers are constructed and analyzed in accordance with this Example 2. Test sections of the diapers exhibit the relative amounts of fluff and superabsorbent material graphically represented in FIG. 19B. In these diapers, the regions having increased levels of superabsorbent are "out of phase" with the regions having increased levels of fluff. The amount of the "out of phase" offset is about three inches.

EXAMPLE 3

Figure 20:
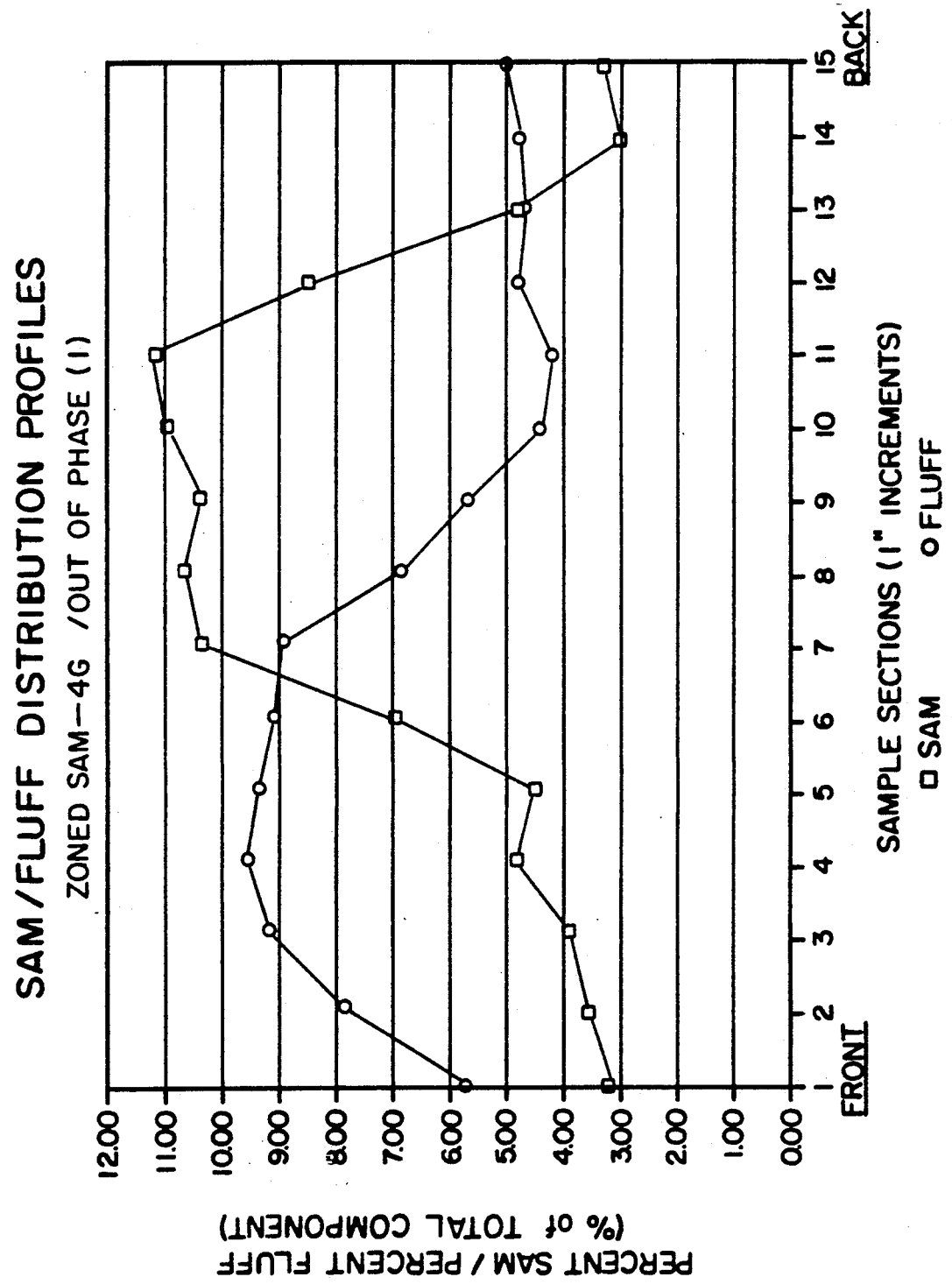
FIGS. 20 and 20A show graphic representations of regions along the length of another article of the invention wherein article regions with higher amounts of superabsorbent are out-of-phase and offset from article regions with higher amounts of fibrous material.
Figure 20A:
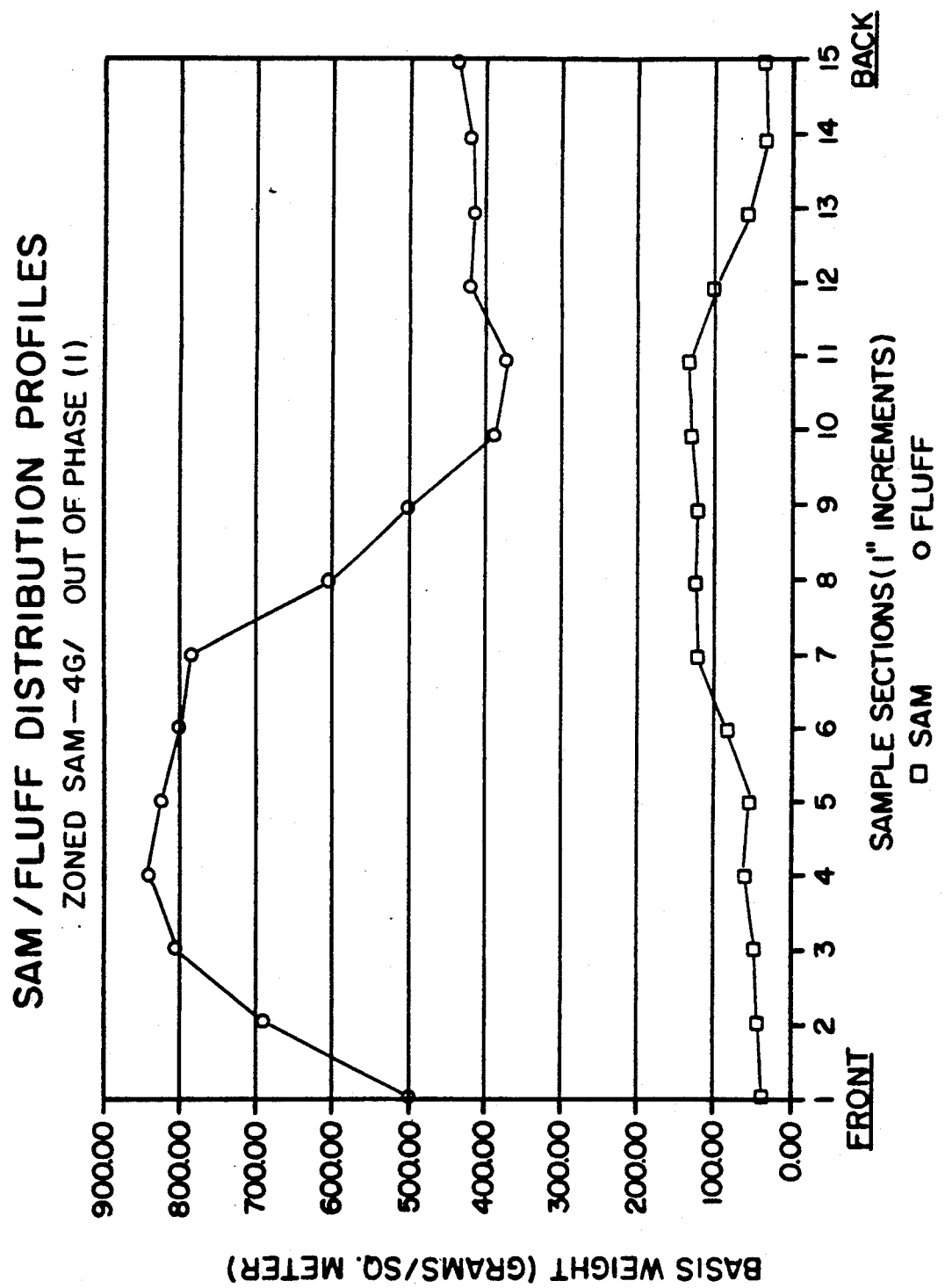

Disposable diapers are constructed in accordance with Example 1. Each of the diapers includes an absorbent body comprising a nonhomogeneous mixture of cellulosic woodpulp fluff and superabsorbent particles composed of sodium polyacrylate superabsorbent hydrogel material (SAM). Test sections of the diapers are analyzed in accordance with Example 1 and exhibit the relative amounts of fluff and superabsorbent material graphically represented in FIGS. 20 and 20A. In this Example, the regions having increased levels of superabsorbent are "out of phase" with the regions having increased levels of fluff by approximately six inches, and are offset towards the rear waistband section of the diaper.

EXAMPLE 4

Figure 21:
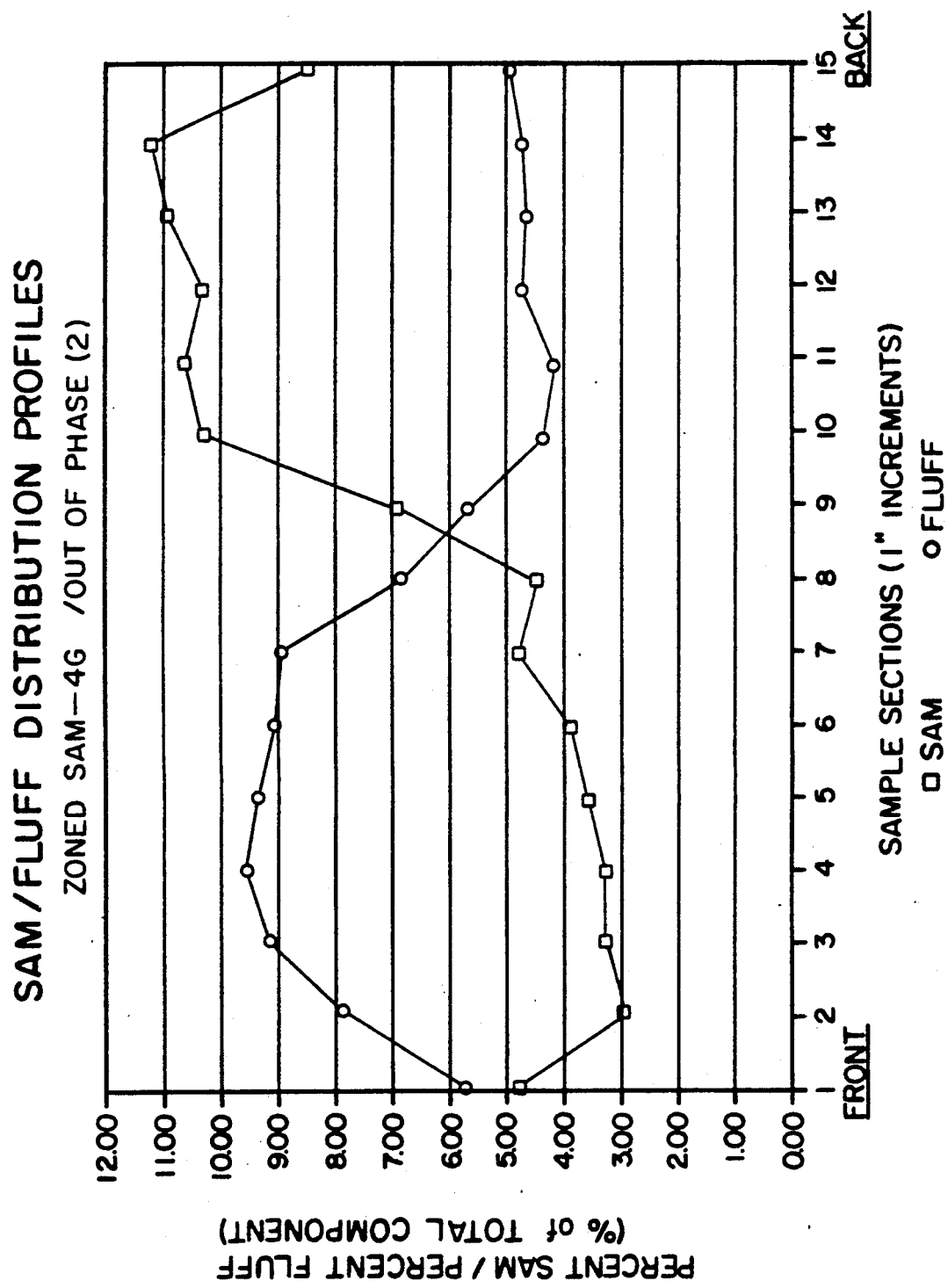
FIG. 21 shows a graphic representation of regions along the length of an article of the invention wherein article regions with higher amounts of superabsorbent are further out-of-phase and offset from article regions with higher amounts of fibrous material.

Disposable diapers are constructed in accordance with Example 1. Each of the diapers includes an absorbent body comprising a nonhomogeneous mixture of cellulosic woodpulp fluff and superabsorbent particles composed of sodium polyacrylate superabsorbent hydrogel material (SAM). Test sections of the diapers are analyzed in accordance with Example 1 and exhibit the relative amounts of fluff and superabsorbent material graphically represented in FIG. 21. In this Example, the regions of increased levels of superabsorbent are "out of phase" with the regions of increased levels of fluff by approximately nine inches and are further offset towards the rear waistband section of the diaper.

Having thus described the invention in rather full detail, it will be readily apparent to a person having ordinary skill in the art that various changes and modifications can be made without departing from the spirit of the invention. All of such changes and modifications are contemplated as being within the scope of the present invention, as defined by the subjoined claims.

We claim:

1. An apparatus for forming a zoned distribution of particulate material within a fibrous web, comprising:
   conveying means for providing a gas entrained supply stream of said particulate material;
   segregating means for centrifugally directing at least a portion of said particulate material into an accumulation region of said apparatus;

transferring means for selectively directing particulate material from said accumulation region into a delivery gas stream to provide an intermittent flow of a selected quantity of particulate material from said accumulation region through a delivery conduit and into a web forming chamber;

fiberizing means for providing a flow of a selected fibrous material into said web forming chamber;

directing means for controlling said intermittent flow of particulate material from said delivery conduit into said forming chamber; and a foraminous forming layer disposed within said forming chamber for receiving said fibrous material and said particulate material to form a fibrous web which includes zoned regions having selected, different amounts of said particulate material therein.

2. An apparatus as recited in claim 1, wherein said segregating means comprises:

a curved conduit having an arcuate bend through which said supply stream moves to operatively concentrate said particulate material toward a radially outward wall of said curved conduit; and means for controlling a velocity of flow of particulate material with said supply stream.

3. An apparatus as recited in claim 2, wherein said curved conduit provides a path having a radius of curvature within the range of about 0.05–5.0 m as measured to said radially outward wall of the conduit.

4. An apparatus as recited in claim 1, wherein said conveying means generates a conveying gas stream for entraining said particulate material and includes a first flow regulating means for providing said conveying gas stream with a gas flow velocity within the range of about 5–45 m/sec.

5. An apparatus as recited in claim 1, further comprising:

means for supplying said delivery gas stream; and second flow regulating means for providing said delivery gas stream with a velocity of gas flow within the range of about 5–45 m/sec.

6. An apparatus as recited in claim 1, further comprising particulate regulating means for providing a selected mass flow rate of particulate material within said supply stream.

7. An apparatus as recited in claim 1, further comprising a particle recovery system.

8. An apparatus as recited in claim 1, wherein said transferring means comprises:

diverting means for selectively directing said particulate material from said curved conduit into said delivery conduit;

controlling means for intermittently operating said diverting means over a selected dwell time period to deliver a controlled quantity of said particulate material into said delivery conduit; and gas delivering means for providing said delivery stream of gas for moving said quantity of particulate material through said delivery conduit.

9. An apparatus as recited in claim 1, wherein said transferring means comprises:

diverting means for selectively directing a quantity of said particulate material from said accumulation region into a receiving chamber;

gas delivering means for providing said delivery stream of gas to move said quantity of particulate material from said receiving chamber and into said delivery conduit; and controlling means for selectively operating said gas delivering means to intermittently move said quantity of particulate material into said delivery conduit.

10. An apparatus as recited in claim 1, further comprising means for directing a substantially continuous stream of particulate material into said web forming chamber.

11. An apparatus as recited in claim 1, comprising a first transferring means for directing a first particulate material into said web forming chamber; and at least a second transferring means for directing a second particulate material into said web forming chamber.

12. An apparatus as recited in claim 11, further comprising means for directing a substantially continuous stream of particulate material into said web forming chamber.

13. An apparatus as recited in claim 1, further comprising flow splitting means for dividing said supply stream of particulate material into two or more substantially separate, supply substreams of particulate material.

14. An apparatus as recited in claim 13, wherein said flow splitting means comprises:

a curved conduit having a radiused bend through which said gas entrained supply stream of particulate material flows to concentrate said particulate material toward a radially outwardly positioned, interior wall member of said curved conduit;

a separating vane member located within an exit zone from said curved conduit and arranged to extend along a line which substantially traverses the cross-section of said conduit exit zone with the major surfaces of said vane member substantially aligned along a longitudinal dimension of said conduit exit zone, said vane member being selectively positionable within said conduit exit zone to divide said supply stream into said supply substreams of particulate material.

15. An apparatus as recited in claim 14, wherein said conduit exit zone has a substantially circular cross-section and said vane member is circumferentially rotatable to provide selective positionability within said conduit exit zone.

16. An apparatus as recited in claim 13, wherein a first substream of the particulate material is directed through a delivery conduit into said web forming chamber; and a second substream of the particulate material is directed to said segregating means.

17. An apparatus as recited in claim 13, wherein a first substream of the particulate material is directed to a first segregating means, and a second substream of the particulate material is directed to a second segregating means.

18. An apparatus as recited in claim 14, wherein each of said first and second segregating means comprises, a curved conduit having an arcuate bend through which a corresponding substream of particulate material moves to operatively concentrate gas entrained particulate material toward a radially outwardly located wall of said curved conduit; and means for controlling a flow velocity of said particulate material within each substream of particulate material.

19. An apparatus as recited in claim 18, wherein said first segregating means has connected thereto a first transferring means, comprising:

diverting means for selectively directing said particulate material from said curved conduit into a delivery conduit;

controlling means for intermittently operating said diverting means over a selected dwell time period to deliver a controlled quantity of said particulate material into said delivery conduit;

gas supplying means for providing a delivery stream of gas for moving said quantity of particulate material through said delivery conduit.

20. An apparatus as recited in claim 1, further comprising a phasing means for sequencing an operation of said transferring means to provide a desired registration between said quantity of particulate material and a selected deposition region along a machine direction of said web.

21. An apparatus as recited in claim 20, wherein said phasing means comprises:

a line shaft encoder which is operably connected to a primary line shaft of the apparatus;

a reference signal generator operably connected to said line shaft to generate a reference pulse per each individual product section intended to be derived from said web; and a programmable controller for receiving and processing outputs from said reference generator and line shaft encoder to selectively sequence the operation of said transferring means.

22. An apparatus as recited in claim 18, wherein said second segregating means has connected thereto a second transferring means, comprising:

diverting means for selectively directing a quantity of said particulate material from said accumulation region into a receiving chamber;

gas delivering means for providing said delivery stream of gas to move said quantity of particulate material from said receiving chamber and into said delivery conduit; and controlling means for selectively operating said gas delivering means to intermittently move said quantity of particulate material into said delivery conduit.

23. An apparatus as recited in claim 22, further comprising a second phasing means for sequencing an operation of said second transferring means to provide a desired registration between a second quantity of particulate material and a selected deposition region along a machine direction of said web.

24. An apparatus as recited in claim 1, further including a particle recovery means for separating said particulate material from a moving mixture of gas and particulate material, said particle recovery means comprising:

a curved conduit having an inlet section and an outlet section;

an exhaust conduit connected to said outlet section to carry gas from said particle recovery means;

a particle reservoir in communication with said outlet section;

pressuring means for providing a gas pressure in said particle reservoir which is relatively higher than a gas pressure in said curved conduit.

* * * * *